(12) United States Patent
Torisawa et al.

(10) Patent No.: US 8,273,735 B2
(45) Date of Patent: Sep. 25, 2012

(54) PROCESS FOR PREPARING BENZAZEPINE COMPOUNDS OR SALTS THEREOF

(75) Inventors: Yasuhiro Torisawa, Tokushima (JP); Kaoru Abe, Tokushima (JP); Yasuaki Muguruma, Tokushima (JP); Shigekazu Fujita, Okazaki (JP); Hidenori Ogawa, Tokushima (JP); Naoto Utsumi, Tokushima (JP); Masahiro Miyake, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 713 days.

(21) Appl. No.: 12/064,178

(22) PCT Filed: Sep. 1, 2006

(86) PCT No.: PCT/JP2006/317804
§ 371 (c)(1),
(2), (4) Date: Aug. 13, 2009

(87) PCT Pub. No.: WO2007/026971
PCT Pub. Date: Mar. 8, 2007

(65) Prior Publication Data
US 2009/0306369 A1 Dec. 10, 2009

(30) Foreign Application Priority Data
Sep. 2, 2005 (JP) ................................. 2005-254744

(51) Int. Cl.
*C07D 223/16* (2006.01)
(52) U.S. Cl. .................................. 514/213.01; 540/593
(58) Field of Classification Search .................. 540/593; 514/213.01
See application file for complete search history.

(56) References Cited

U.S. PATENT DOCUMENTS

| 3,965,144 A | | 6/1976 | Packard et al. | |
|---|---|---|---|---|
| 4,410,520 A | | 10/1983 | Watthey | |
| 5,559,230 A | * | 9/1996 | Ogawa et al. | 540/569 |
| 5,827,862 A | * | 10/1998 | Yamamura et al. | 514/312 |

FOREIGN PATENT DOCUMENTS

| JP | 06-080641 | 3/1994 |
|---|---|---|
| JP | 09-168396 | 6/1997 |
| WO | WO 91/05549 | 5/1991 |

OTHER PUBLICATIONS

Chinese Office Action dated Jul. 22, 2011.

Neubert, Mary E., and Fishel, D.L., "Preparation of 4-Alkyl-and 4-Halobenzoyl Chlorides: 4-Pentylbenzoyl Chloride," Organic Syntheses, Coll. Vo. 7, p. 420 (1990); vol. 61, p. 8 (1983).
Hidenori Ogawa et al., "Orally Active, Nonpeptide Vasopressin $V_2$ Receptor Antagonists: A Novel Series of 1-[4-(Benzoylamino)benzoyl]-2,3,4,5-tetrahydro-1H-benzazepines and Related Compounds," Journal of Medicinal Chemistry vol. 39, No. 18, pp. 3547-3555.
Kenji Otsubo, "Studies on the Efficient Syntheses of the Drug Metabolites," Yakugaku Zasshi 120 (11) 1135-1147 (2000).
Jun Matsubara et al., "Enanthioselective Synthesis of the Metabolites of Vasopressin $V_2$ Receptor Antagonist OPC-31260 via Lipase-Catalyzed Transesterification," Tetrahedron 56 (2000) 4667-4682.
Ian P. Andrews et al., "A new synthesis of the CPIIb/IIIa receptor antagonist SB-214857-A," Tetrahedron Letters 42 (2001) 4915-4917.
Yasuhiro Torisawa et al., "Beneficial Effect of Cesium Salts on Pd-Catalyzed Hydroxycarbonylation," Bioorganic & Medicinal Chemistry Letters 10 (2000) 2493-2495.
Database Beilstein Crossfire, Beilstein Institute of Organic Chemistry, Reaction ID: 388325, XP-002419872, abstract.
L.H. Werner et al., "The Alkaloids of Tabernanthe Iboga. VII. Derivatives of Isoquinuclidine," Journal of the American Chemical Society vol. 80, 1958, 2733-2736.
René Royer et al., "Synthesis of 1,4-Diacylbenzenes by Thermal Decomposition of α-(4'-Acylphenoxy)propiophenones," Journal of Organic Chemistry vol. 26, 1961, 4308-4311.
Kazumi Kondo et al., "7-Chloro-5-hydroxy-1-[2-methyl-4-(2-methylbenzoylamino)benzoyl]-2,3,4,5-tetrahydro-1H-1-benzazepine (OPC-41061): A Potent, Orally Active Nonpeptide Arginine Vasopressin $V_2$ Receptor Antagonist," Bioorganic & Medicinal Chemistry 7 (1999), 1743-1754.

* cited by examiner

*Primary Examiner* — Bruck Kifle
(74) *Attorney, Agent, or Firm* — Finnegan, Henderson, Farabow, Garrett & Dunner, L.L.P.

(57) ABSTRACT

This invention provides a process for preparing benzazepine compounds of the formula (1): wherein $X^1$ is a halogen atom, $R^1$ and $R^2$ are a lower alkyl group, or salts thereof as well as intermediate benzoic acid compounds in high yield and high purity on industrial scale, which are useful as an intermediate for preparing a pharmaceutically active 2,3,4,5-tetrahydro-1H-1-benzazepine compound having vasopressin antagonistic activity.

(1)

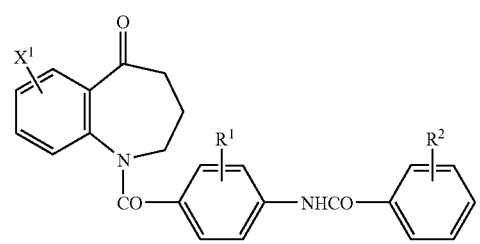

11 Claims, No Drawings

PROCESS FOR PREPARING BENZAZEPINE COMPOUNDS OR SALTS THEREOF

TECHNICAL FIELD

The present invention is concerned with a process for preparing benzazepine compounds or salts thereof as well as the intermediate compounds or salts thereof. More particularly, it relates to a process for preparing benzazepine compounds of the formula (1):

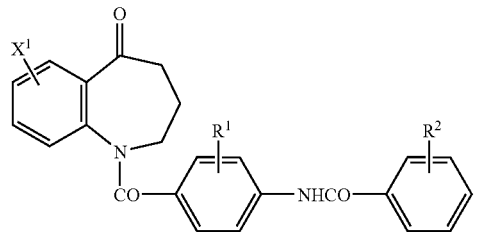

wherein $X^1$ is a halogen atom, $R^1$ and $R^2$ are independently a lower alkyl group, or salts thereof (hereinafter, these compounds including salts are occasionally referred to as "benzazepine compounds (1)" or simply as "compounds (1)"), and an intermediate compound, benzoic acid compounds of the formula (4):

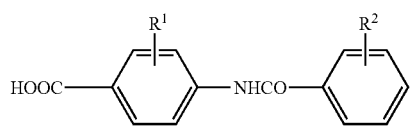

wherein $R^1$ and $R^2$ are as defined above, or salts thereof (hereinafter, these compounds including salts are occasionally referred to as "benzoic acid compounds (4)" or simply as "compounds (4)").

BACKGROUND ART

It is known that the benzazepine compounds of the above formula (1) or salts thereof are useful as an intermediate for preparing a pharmaceutically active benzazepine compound having vasopressin antagonistic activity, e.g. the compounds (10) as mentioned hereinafter (cf. JP-A-4-154765).

It is also known that the benzazepine compounds (1) have been prepared by the processes as shown in the following Reaction schemes A and B (cf. JP-A-4-154765 and Kazumi Kondo et al., Bioorganic & Medicinal Chemistry 7 (1999), pp. 1743-1754).

Reaction Scheme A:

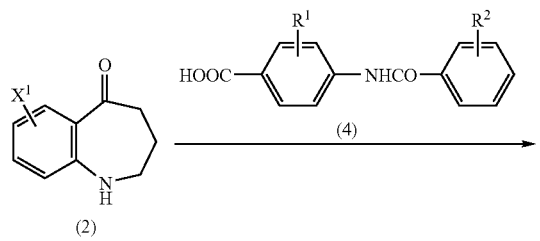

Reaction Scheme B:

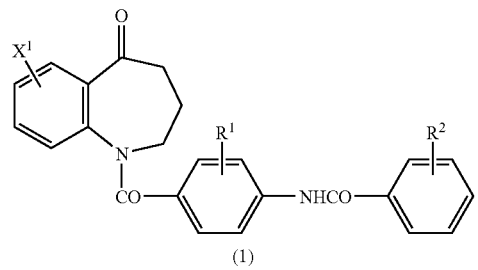

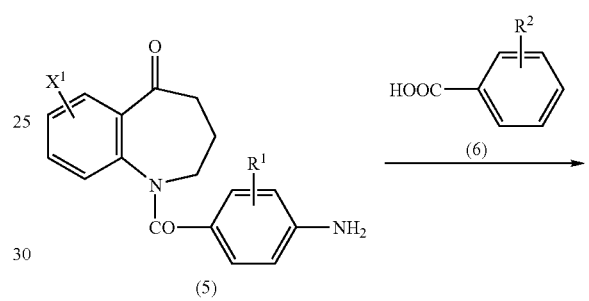

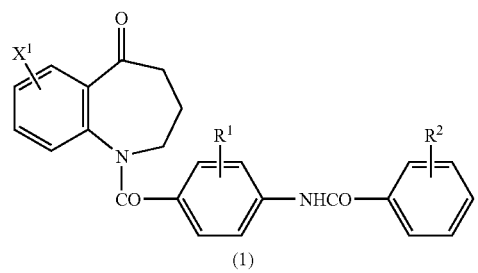

wherein $R^1$, $R^2$ and $X^1$ are as defined above.

However, the methods shown in the above Reaction Schemes A and B are not suitable for producing the desired compounds (1) on industrial scale. That is, the starting compound (4) to be used in Reaction Scheme A is hardly obtainable in high yield and in high purity, and hence, the method of Reaction Scheme A is not suitable as an industrial process. Besides, the method of Reaction Scheme B can not give the desired compounds (1) in high yield and in high purity, and hence it is not suitable as an industrial process.

It is further known that the benzoic acid compounds of the above formula (4) are useful as an intermediate for preparing a pharmaceutically active benzazepine compound having vasopressin antagonistic activity (cf. JP-A-4-154765). The benzoic acid compounds (4) are usually prepared by a process as shown in the following Reaction Scheme C (cf. Yasuhiro Torisawa et al., Bioorganic & Medicinal Chemistry Letters, 10 (2000), pp. 2493-2495).

Reaction Scheme C:

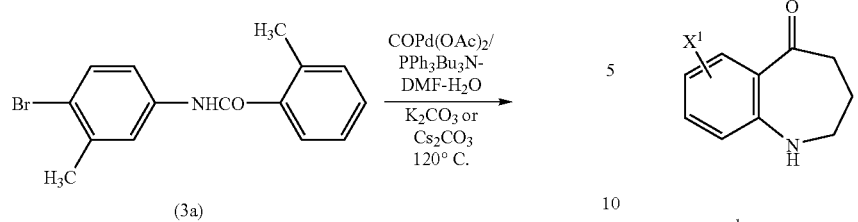

(3a)

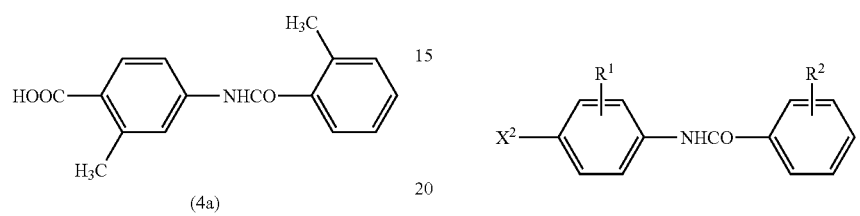

(4a)

DISCLOSURE OF INVENTION

An object of the invention is to provide an improved process for producing the benzazepine compounds (1), which can give the desired compounds in high yield and in high purity on industrial scale and hence is suitable as an industrial process for producing the benzazepine compounds (1).

Another object of the invention is to provide a process for producing the intermediate benzoic acid compounds (4) in high yield and in high purity on industrial scale.

A further object of the invention is to provide a process for producing the pharmaceutically active compounds (10) as defined hereinafter in high yield and in high purity on industrial scale.

After intensively studying, the present inventors have found that the desired compounds of the formulae (1), (4) and (10) or salts thereof can be produced in high yield and in high purity on industrial scale by the processes as mentioned below.

Thus, the present invention includes the following features.

1. A process for producing a benzazepine compound of the formula (1):

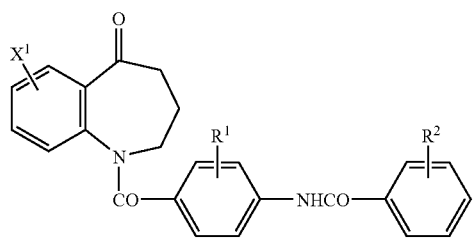

(1)

wherein $X^1$ is a halogen atom, $R^1$ and $R^2$ are independently a lower alkyl group, or salts thereof, which comprises reacting a benzazepine compound of the formula (2):

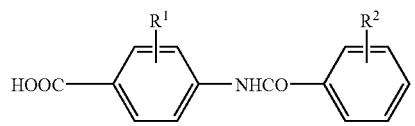

(2)

wherein $X^1$ is as defined above, or a salt thereof with an amide compound of the formula (3):

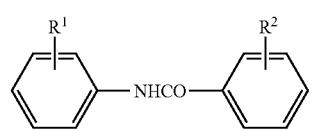

(3)

wherein $R^1$ and $R^2$ are as defined above and $X^2$ is a halogen atom, or a salt thereof in the presence of a carbonylating agent.

2. A process for producing a benzoic acid compound of the formula (4):

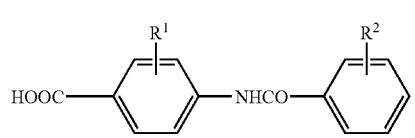

(4)

wherein $R^1$ and $R^2$ are as defined above, or a salt thereof, which comprises reacting an amide compound of the formula (11):

(11)

wherein $R^1$ and $R^2$ are as defined above, or a salt thereof, with a compound of the formula (19):

$$X^6COCOX^7 \quad (19)$$

wherein $X^6$ and $X^7$ are independently a halogen atom.

3. A process for producing a benzoic acid compound of the formula (4):

(4)

wherein $R^1$ and $R^2$ are as defined above, or a salt thereof, which comprises oxidizing an amide compound of the formula (12):

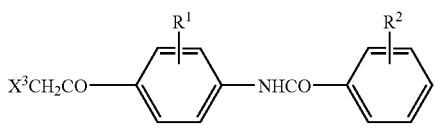

wherein $R^1$ and $R^2$ are as defined above and $X^3$ is a halogen atom, or a salt thereof.

4. A process for producing a benzoic acid compound of the formula (4):

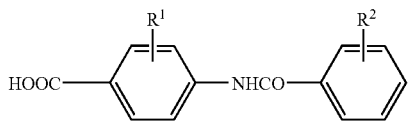

wherein $R^1$ and $R^2$ are as defined above, or a salt thereof, which comprises hydrolyzing an amide compound of the formula (13):

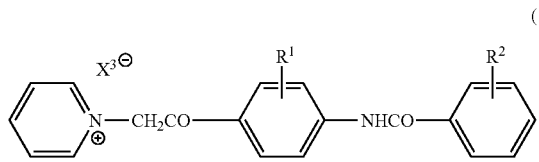

wherein $R^1$, $R^2$ and $X^3$ are as defined above, or a salt thereof.

5. A process for producing a benzoic acid compound of the formula (4):

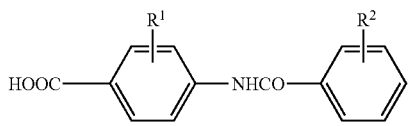

wherein $R^1$ and $R^2$ are as defined above, or a salt thereof, which comprises oxidizing an amide compound of the formula (14):

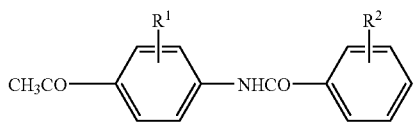

wherein $R^1$ and $R^2$ are as defined above, or a salt thereof.

6. A process for producing a 2,3,4,5-tetrahydro-1H-1-benzazepine compound of the formula (10):

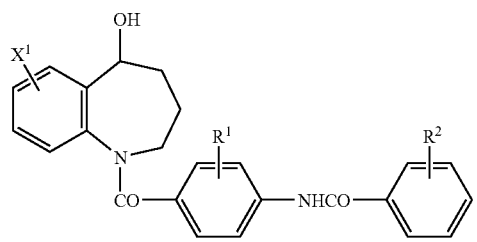

wherein $R^1$, $R^2$ and $X^1$ are as defined above, or a salt thereof, which comprises reducing a benzazepine compound of the formula (1):

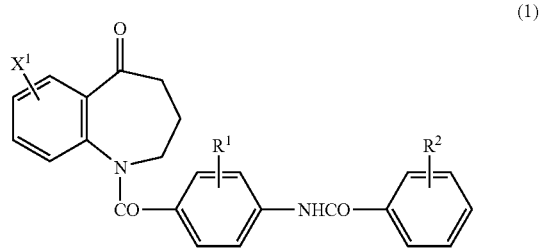

wherein $R^1$, $R^2$ and $X^1$ are as defined above, or a salt thereof in the presence of a hydrogenating agent in an amount of 0.1 to 1 mole per 1 mole of the compound (1).

7. The process according to the above 6, wherein the hydrogenating agent is a member selected from the group consisting of lithium aluminum hydride, sodium borohydride, zinc borohydride, and diborane.

8. The process according to the above 7, wherein the hydrogenating agent is sodium borohydride which is used in an amount of 0.25 to 1 mole per 1 mole of the compound (1).

9. The process according to the above 8, wherein the hydrogenating agent is used in an amount of 0.25 to 0.5 mole per 1 mole of the compound (1).

10. The process according to the above 1, wherein the benzazepine compound (1) is 7-chloro-1-[2-methyl-4-(2-methylbenzoylamino)benzoyl]-2,3,4,5-tetrahydro-1H-1-benzazepin-5-one, or a salt thereof.

11. The process according to any one of the above 6 to 9, wherein the 2,3,4,5-tetrahydro-1H-1-benzazepine compound (10) is 7-chloro-5-hydroxy-1-[2-methyl-4-(2-methylbenzoylamino)benzoyl]-2,3,4,5-tetrahydro-1H-1-benzazepine, or a salt thereof.

DETAILED DESCRIPTION OF THE INVENTION

The desired compounds of the formulae (1), (4) and (10) or salts thereof can be produced in high yield and in high purity on industrial scale by the processes as mentioned below.

Production of Compounds (1):

The desired benzazepine compounds (1) or salts thereof can be prepared by a process comprising reacting a compound of the formula (2) (hereinafter, occasionally referred to as "compound (2)") or a salt thereof with an amide compound of the formula (3) (hereinafter, occasionally referred to as "compound (3)") or a salt thereof in the presence of a carbonylating agent as shown in the following Reaction Scheme I.

Reaction Scheme I:

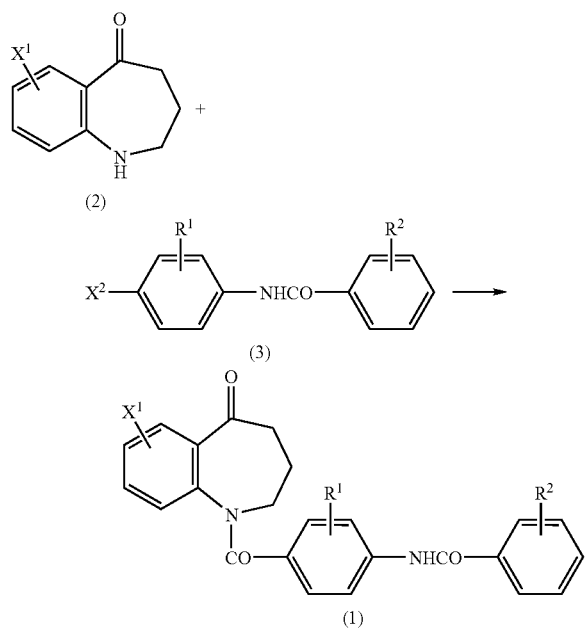

wherein $R^1$, $R^2$ and $X^1$ are as defined above.

The starting compound (2) or a salt thereof may be produced by any known process as mentioned below. In said compound (2), the halogen atom of $X^1$ is not specified but may include fluorine atom, chlorine atom, bromine atom and iodine atom, preferably fluorine atom or chlorine atom.

The compound (2) or a salt thereof can readily be produced, for example, from a benzazepine compound of the formula (7) or a salt thereof, as shown in the following Reaction Scheme II.

Reaction Scheme II:

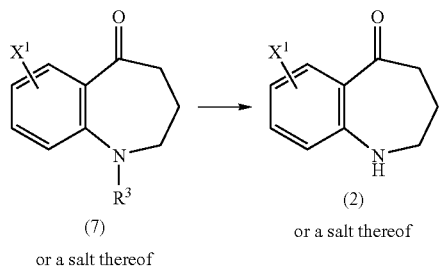

wherein $X^1$ is as defined above, and $R^3$ is a phenylsulfonyl group having optionally a lower alkyl substituent on the phenyl ring.

The phenylsulfonyl group having optionally a lower alkyl substituent on the phenyl ring denotes a phenylsulfonyl group having optionally one to three substituents of a straight chain or branched chain alkyl having 1 to 6 carbon atoms on the phenyl ring, such as phenylsulfonyl, 2-methylphenylsulfonyl, 3-methylphenylsulfonyl, 4-methylphenylsulfonyl, 2-ethylphenylsulfonyl, 3-n-propylphenylsulfonyl, 4-n-butylphenylsulfonyl, 2-n-pentylphenylsulfonyl, 3-n-hexylphenylsulfonyl, 2,3-dimethylphenylsulfonyl, 2,4,6-trimethylphenylsulfonyl.

The compound (2) or a salt thereof can be prepared by treating the benzazepine compound of the formula (7) or a salt thereof with sulfuric acid.

The salt of benzazepine compound (7) can be prepared by reacting the benzazepine compound (7) with a pharmaceutically acceptable acidic or basic compound, for example, an inorganic acid (e.g. hydrochoric acid, hydrobromic acid, nitric acid, sulfuric acid, phosphoric acid), an organic acid (e.g. methanesulfonic acid, ethanesulfonic acid, p-toluenesulfonic acid, acetic acid, citric acid, tartaric acid, oxalic acid, maleic acid, fumaric acid, malic acid, succinic acid, benzoic acid). The basic compound includes, for example, sodium hydroxide, potassium hydroxide, lithium hydroxide, calcium hydroxide, sodium carbonate, potassium carbonate, sodium hydrogen carbonate, potassium hydrogen carbonate.

The sulfuric acid is not limited to any specific concentration but is usually used in a concentration of 50% by weight or higher. it includes concentrated sulfuric acid, Preferred concentration of sulfuric acid is in the range of 85 to 98% by weight.

The treatment of the compound (7) or a salt thereof with sulfuric acid is usually carried out at a temperature of 0° C. to 150° C., preferably 0° C. to 100° C., and the reaction time is optionally determined depending on the reaction temperature, preferably in the range of about 0.5 to about 5 hours.

After the reaction, the desired compound (2) or a salt thereof can be isolated from the reaction mixture by a conventional isolation method, for example, by cooling the reaction mixture, filtering, concentrating, and extracting the product. The product may further be purified by a conventional purification method, such as column chromatography, recrystallization. The recrystallization may be done by using a seed crystal, or alternatively may be done with active carbon.

When the compound (2) is obtained in the form of a free base in the above reaction of Reaction Scheme II, it may be converted into a salt with a pharmaceutically acceptable acidic or basic compound. The acidic compound includes, for example, an inorganic acid (e.g. hydrochloric acid, hydrobromic acid, nitric acid, sulfuric acid, phosphoric acid), an organic acid (e.g. methanesulfonic acid, ethanesulfonic acid, p-toluenesulfonic acid, acetic acid, citric acid, tartaric acid, oxalic acid, maleic acid, fumaric acid, malic acid, succinic acid, benzoic acid). The basic compound includes, for example, sodium hydroxide, potassium hydroxide, lithium hydroxide, calcium hydroxide, sodium carbonate, potassium carbonate, sodium hydrogen carbonate, potassium hydrogen carbonate.

In another starting compound, the amide compound (3) or a salt thereof in the above Reaction Scheme I, $X^2$ is not limited to any specific halogen atom, but includes fluorine atom, chlorine atom, bromine atom or iodine atom, among which particularly preferred one is bromine atom or iodine atom.

The $R^1$ and $R^2$ in the compound (3) are not limited to any specific lower alkyl group but include a straight chain or branched chain alkyl having 1 to 6 carbon atoms, for example, methyl, ethyl, propyl, isopropyl, butyl, tert-butyl, pentyl, or hexyl group. Preferred $R^1$ is methyl group, and preferred $R^2$ is methyl group.

The compound (3) or a salt thereof can be produced by a known method, for example, from an amide compound of the formula (8) or a salt thereof as shown in the following Reaction Scheme III.

Reaction Scheme III:

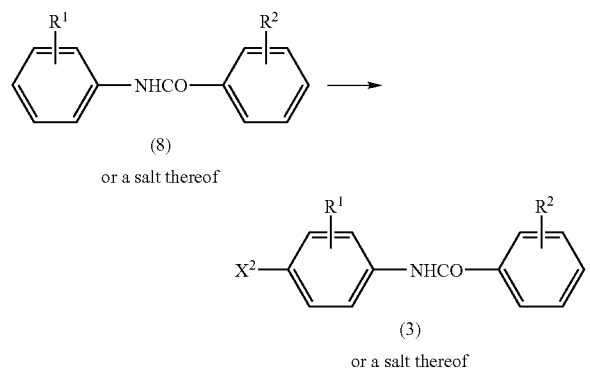

(8)

or a salt thereof (3)

or a salt thereof wherein $R^1$, $R^2$ and $X^2$ are as defined above.

That is, the compound (3) or a salt thereof can be obtained by treating the amide compound (8) or a salt thereof with a halogenating agent in a solvent.

The salt of amide compound (8) can be prepared by reacting the amide compound (8) with a pharmaceutically acceptable acidic or basic compound, for example, an inorganic acid (e.g. hydrochoric acid, hydrobromic acid, nitric acid, sulfuric acid, phosphoric acid), an organic acid (e.g. methanesulfonic acid, ethanesulfonic acid, p-toluenesulfonic acid, acetic acid, citric acid, tartaric acid, oxalic acid, maleic acid, fumaric acid, malic acid, succinic acid, benzoic acid). The basic compound includes, for example, sodium hydroxide, potassium hydroxide, lithium hydroxide, calcium hydroxide, sodium carbonate, potassium carbonate, sodium hydrogen carbonate, potassium hydrogen carbonate.

The halogenating agent includes, for example, a halogen molecule (e.g. bromine, chlorine), a chloride compound (e.g. iodine chloride, sulfuryl chloride), a copper compound (e.g. cuprous bromide), an N-halogenated succinimide (e.g. N-bromosuccinimide), or the like. The halogenating agent is not limited to any specific amount but is usually used in an amount of 1 mole to 10 moles, preferably 1 mole to 5 moles, per 1 mole of the compound (8).

The solvent includes, for example, ethers (e.g. diethyl ether, tetrahydrofuran, dioxane, 2-methoxyethanol, monoglyme, diglyme), halogenated hydrocarbons (e.g. dichloromethane, dichloroethane, chloroform, carbon tetrachloride), fatty acids (e.g. acetic acid, propionic acid), carbon disulfide, or a mixture of the above solvents.

The reaction temperature is not specified but is usually in the range of 0° C. to 100° C., preferably 0° C. to 50° C., and the reaction time is optionally determined depending on the kinds of the starting compound, and other reaction conditions, but is usually in the range of about 5 minutes to about 30 hours.

After the reaction, the desired compound (3) or a salt thereof can be isolated from the reaction mixture by a conventional isolation method, for example, by cooling the reaction mixture, filtering, concentrating, and extracting the product. The product may further be purified by a conventional purification method, such as column chromatography, recrystallization. The recrystallization may be done by using a seed crystal, or alternatively may be done with active carbon.

When the compound (3) is obtained in the form of a free base in the above reaction of Reaction Scheme III, it may be converted into a salt with a pharmaceutically acceptable acidic or basic compound. The acidic compound includes, for example, an inorganic acid (e.g. hydrochloric acid, hydrobromic acid, nitric acid, sulfuric acid, phosphoric acid), an organic acid (e.g. methanesulfonic acid, ethanesulfonic acid, p-toluenesulfonic acid, acetic acid, citric acid, tartaric acid, oxalic acid, maleic acid, fumaric acid, malic acid, succinic acid, benzoic acid). The basic compound includes, for example, sodium hydroxide, potassium hydroxide, lithium hydroxide, calcium hydroxide, sodium carbonate, potassium carbonate, sodium hydrogen carbonate, potassium hydrogen carbonate.

The desired compound (1) or a salt thereof can be produced by reacting the compound (2) with the compound (3) in the presence of a carbonylating compound as shown in Reaction Scheme-I.

The amount of the compound (3) is not specified, but is usually at least equimolar amount, preferably 1 to 2 moles, per 1 mole of the compound (2).

The carbonylating agent is not limited but includes, for example, carbon monoxide, a metal carbonyl (e.g., $Cr(CO)_6$, $Mo(CO)_6$, $W(CO)_6$), or the like. The amount of the carbonylating agent may be not specified as far as it is at least equimolar amount to the compound (2), but it is preferably used in a far excess amount to the compound (2).

When a carbon monoxide is used as the carbonylating agent, the reaction is preferably carried out in the presence of a phosphoric compound and a palladium compound as a catalyst.

The phosphoric compound includes a compound of the formula (9):

(9)

wherein $R^4$, $R^5$ and $R^6$ are the same or different and are each a lower alkyl group, a cycloalkyl group, a phenyl group, a pyridyl group, or a phenyl-lower alkyl group (hereinafter, it may be occasionally referred to as "compound (9)").

The lower alkyl group for $R^4$, $R^5$ and $R^6$ is not specified but includes a straight chain or branched chain alkyl group having 1 to 6 carbon atoms, for example, methyl, ethyl, propyl, isopropyl, butyl, tert-butyl, pentyl, or hexyl group.

The cycloalkyl group is not specified but includes a cycloalkyl group having 3 to 8 carbon atoms, for example, cyclopropyl, cyclobutyl, cyclopentyl, cyclohexyl, cycloheptyl or cyclooctyl group.

The phenyl group may optionally have a substituent on the phenyl ring. The substituent on the phenyl ring includes, for example, a lower alkyl group, a lower alkoxy group, a sulfo group, a carboxyl group, a hydroxy group, an amino group, a polymer residue. The lower alkyl group includes a straight chain or branched chain alkyl group having 1 to 6 carbon atoms, for example, methyl, ethyl, n-propyl, isopropyl, n-butyl, tert-butyl, n-pentyl, or n-hexyl group. The lower alkoxy group includes a straight chain or branched chain alkoxy group having 1 to 6 carbon atoms, for example, methoxy, ethoxy, n-propoxy, isopropoxy, n-butoxy, isobutoxy, sec-butoxy, tert-butoxy, n-pentyloxy, or n-hexyloxy group. The amino group includes an amino group having optionally one or two of a straight chain or branched chain alkyl group having 1 to 6 carbon atoms, for example, amino, N-methylamino, N-ethylamino, N-propylamino, N-butylamino, N-pentylamino, N-hexylamino, N,N-dimethylamino, N-methyl-N-ethylamino group. The polymer residue includes a residue of a polystyrene resin.

The phenyl-lower alkyl group includes a phenylalkyl group wherein the alkyl moiety is a straight chain or branched chain alkyl group having 1 to 6 carbon atoms, for example, benzyl, 1-phenethyl, 2-phenethyl, 3-phenylpropyl, 2-phenylpropyl, 4-phenylbutyl, 5-phenylpentyl, 4-phenylpentyl, 6-phenylhexyl, 2-methyl-3-phenylpropyl, 1,1-dimethyl-2-phenylethyl group, or the like. The phenyl-lower alkyl group may optionally have a substituent on the phenyl ring. Said substituent may be the same as the above-mentioned substituents on phenyl group.

The examples of the compound (9) are 4-(dimethylamino)phenyldiphenylphosphine, diphenyl-2-pyridylphosphine, tricyclohexylphosphine, 4-diphenylphosphino-polystyrene resin, 4-diphenylphosphino-methylpolystyrene resin, or the like.

The palladium compound is not specified but includes, for example, palladium acetate, palladium chloride, palladium bromide, palladium-carbon, tetrakis(triphenylphosphine)-palladium, or the like.

The amount of the compound (9) is not specified but it is usually in the range of 0.005 to 1 mole, preferably 0.01 to 0.5 mole, per 1 mole of the compound (3). The amount of the palladium compound is not specified but it is usually in the range of 0.001 to 0.5 mole, preferably 0.01 to 0.25 mole, per 1 mole of the compound (3).

The reaction for producing the compound (1) or a salt thereof is preferably carried out in a solvent. The solvent includes, for example, alcohols (e.g. tert-butanol), halogenated hydrocarbons (e.g. chloroform, dichloromethane, dichloroethane, carbon tetrachloride), aromatic hydrocarbons (e.g. benzene, toluene, xylene), ethers (e.g. diethyl ether, diisopropyl ether, tetrahydrofuran, dimethoxyethane, cyclopentyl methyl ether), esters (e.g. methyl acetate, ethyl acetate, isopropyl acetate, butyl acetate), aprotic polar solvents (e.g. N,N-dimethylformamide, dimethyl sulfoxide, hexamethylphosphoric triamide, acetonitrile, pyridine, acetone, N-methylpyrrolidone, N—N-dimethylacetamide, 1,3-dimethylimidazolidinone, N,N-dimethylpropyleneurea, or the like. These solvents may be used alone or in a mixture of two or more thereof.

The above reaction for the production of the compound (1) or a salt thereof is preferably carried out in the presence of a basic compound. The basic compound is not specified but includes organic bases and inorganic bases. The organic bases are, for example, triethylamine, trimethylamine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), cesium acetate, or the like. Inorganic bases are, for example, carbonates (e.g. cesium carbonate, cesium hydrogen carbonate, sodium carbonate, potassium carbonate, sodium hydrogen carbonate, potassium hydrogen carbonate), hydroxides (e.g. sodium hydroxide, potassium hydroxide, calcium hydroxide), hydrides (e.g. potassium hydride, sodium hydride), salts of alkali metal (e.g. potassium, sodium), amide salts (sodium amide, potassium amide). These basic compounds may be used alone or in a mixture of two or more thereof. Among these basic compounds, organic bases are preferable, particularly preferred ones are N-ethyldiisopropylamine, 1,8-diazabicyclo[5.4.0]undecene-7 (DBU).

The reaction temperature is not specified but is usually in the range of 25° C. to 200° C., preferably 60° C. to 150° C., and the reaction time is optionally determined depending on the reaction temperature or other conditions, but is preferably in the range of about 1 to about 10 hours.

The salts of the benzazepine compounds (1) include acid addition salts of the benzazepine compounds (1). These acid addition salts can be prepared by treating the benzazepine compound (1) with a pharmaceutically acceptable acidic compound. The acidic compound includes, for example, an inorganic acid (e.g. hydrochloric acid, hydrobromic acid, nitric acid, sulfuric acid, phosphoric acid), an organic acid (e.g. methanesulfonic acid, ethanesulfonic acid, p-toluenesulfonic acid, acetic acid, citric acid, tartaric acid, oxalic acid, maleic acid, fumaric acid, malic acid, succinic acid, benzoic acid).

The compound (1) can readily be converted into a salt by treating it with a pharmaceutically acceptable basic compound. The basic compound includes, for example, sodium hydroxide, potassium hydroxide, lithium hydroxide, calcium hydroxide, sodium carbonate, potassium carbonate, sodium hydrogen carbonate, potassium hydrogen carbonate.

When a salt of the compound (2) and/or a salt of the compound (3) are/is used, the desired compound (1) is also obtained in the form of a salt.

After the reaction, the desired compound (1) can be isolated from the reaction mixture by a conventional isolation method, for example, by cooling the reaction mixture, filtering, concentrating, and extracting the product. The product may further be purified by a conventional purification method, such as column chromatography, recrystallization. The recrystallization may be done by using a seed crystal, or alternatively may be done with active carbon.

Production of Compounds (10):

The compounds (1) obtained above can be converted into 2,3,4,5-tetrahydro-1H-1-benzazepine compounds of the formula (10) which are useful as a vasopressin antagonist. That is, the compound (10) or a salt thereof can be produced by reducing the compound (1) or a salt with a hydrogenating agent as shown in the following Reaction Scheme-IV.

Reaction Scheme-IV:

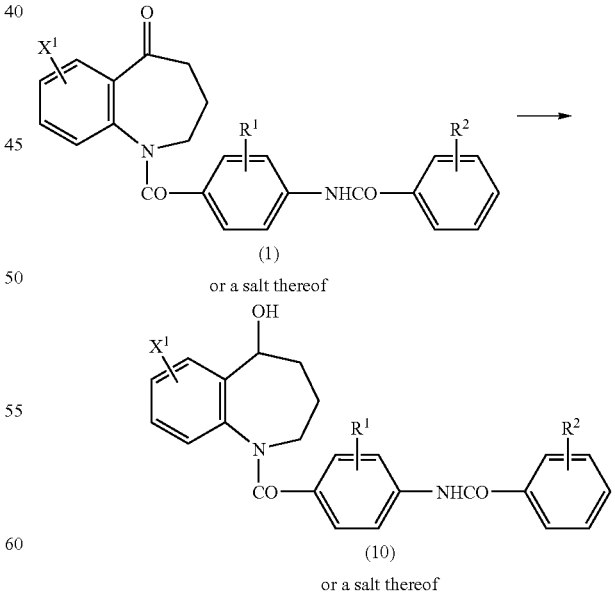

wherein $R^1$, $R^2$ and $X^1$ are as defined above.

The reduction reaction of the compound (1) in the above Reaction Scheme-IV is not specified, but is preferably carried out by using a hydrogenating agent, particularly preferably by using the hydrogenating agent in an amount of equimolar or less amount to the compound (1) in view of producing the compound (10) in high yield and in high purity, because the hydrogenating reaction of the present invention can proceed with hardly occurring undesirable dehalogenating reaction which has been occurred in the known processes.

The hydrogenating agent includes, for example, aluminum lithium hydride, sodium borohydride, zinc borohydride, diborane, or the like. These hydrogenating agents may be used alone or in a mixture of two or more thereof. The hydrogenating agent is used in an amount of equimolar or less to the compound (1) for producing the desired compound (10) in high yield and high purity as mentioned above. Thus, the hydrogenating agent is usually used in an amount of 0.1 to 1 mole, preferably 0.25 to 1 mole, more preferably 0.25 to 0.5 mole, per 1 mole of the compound (1). The reducing reaction is usually carried out in a solvent. The solvent includes, for example, water, lower alcohols (e.g. methanol, isopropanol), ethers (e.g. tetrahydrofuran, diethyl ether, diisopropyl ether, diglyme), or the like. These solvents may be used alone or in a mixture of two or more thereof. When aluminum lithium hydride or diborane is used as the reducing agent, it is preferable to use an anhydrous solvent such as tetrahydrofuran, diethyl ether, isopropyl ether, or diglyme.

The reaction temperature is not specified but is usually in the range of −60° C. to 150° C., preferably −30° C. to 100° C., and the reaction time is optionally determined depending on the reaction temperature or other conditions, but is preferably in the range of about 10 minutes to about 15 hours.

After the reaction, the desired compound (10) can be isolated from the reaction mixture by a conventional isolation method, for example, by cooling the reaction mixture, filtering, concentrating, and extracting the product. The compound (10) or a salt thereof may further be purified by a conventional purification method, such as column chromatography, recrystallization. The recrystallization may be done by using a seed crystal, or alternatively may be done with active carbon.

When the compound (10) is obtained in the form of a free base in the above reaction of Reaction Scheme-IV, the compound (10) can readily be converted into a salt by treating it with a pharmaceutically acceptable acidic compound or basic compound. The acidic compound includes, for example, an inorganic acid (e.g. hydrochloric acid, hydrobromic acid, nitric acid, sulfuric acid, phosphoric acid), an organic acid (e.g. methanesulfonic acid, ethanesulfonic acid, p-toluenesulfonic acid, acetic acid, citric acid, tartaric acid, oxalic acid, maleic acid, fumaric acid, malic acid, succinic acid, benzoic acid). The basic compound includes, for example, sodium hydroxide, potassium hydroxide, lithium hydroxide, calcium hydroxide, sodium carbonate, potassium carbonate, sodium hydrogen carbonate, potassium hydrogen carbonate.

Production of Compounds (4):

The intermediate benzoic acid compounds for the formula (4) or a salt thereof can be prepared by various methods, (1) by reacting an amide compound (11) or a salt thereof with an oxalyl halide, e.g. a compound of the formula (19); (2) by oxidizing an amide compound (12) or a salt thereof; (3) by hydrolyzing an amide compound (13) or a salt thereof; or (4) by oxidizing an amide compound (14) or a salt thereof as shown in the following Reaction Scheme-V.

Reaction Scheme-V:

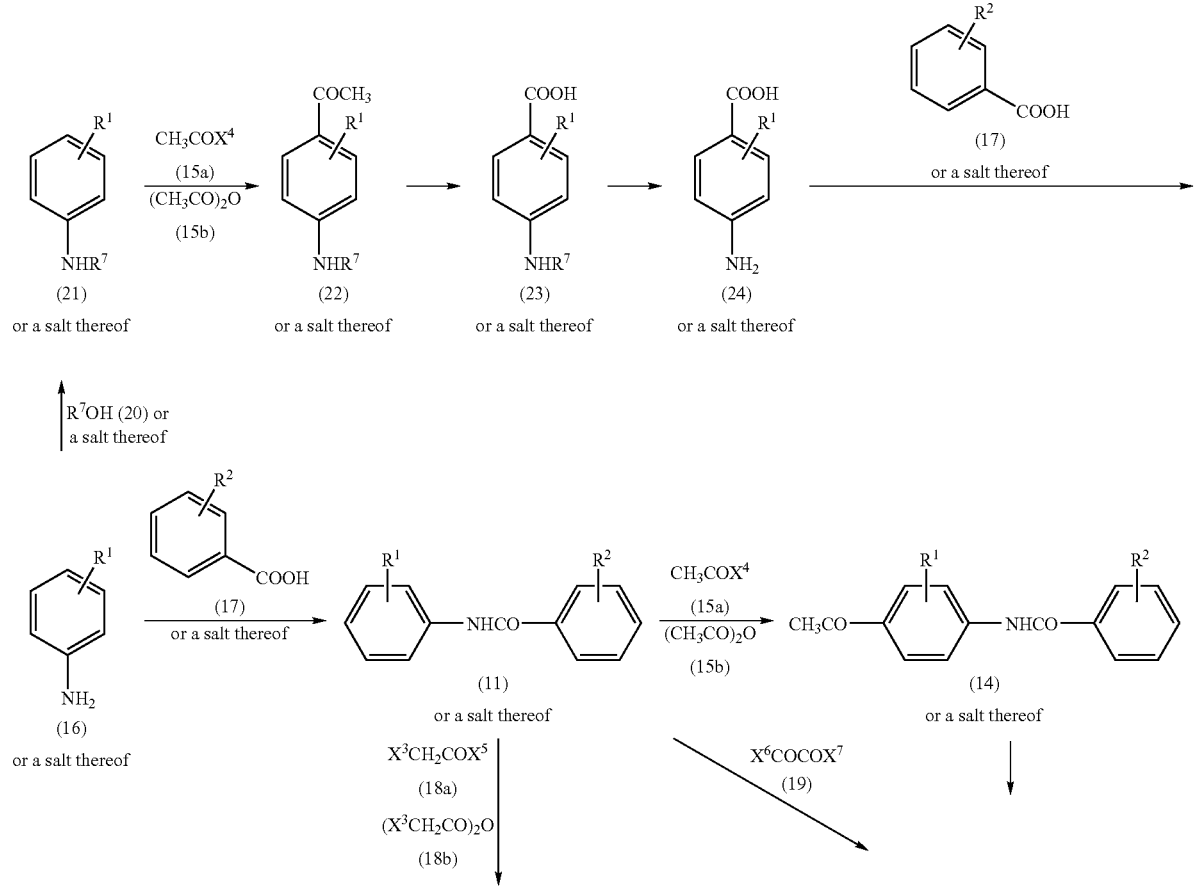

-continued

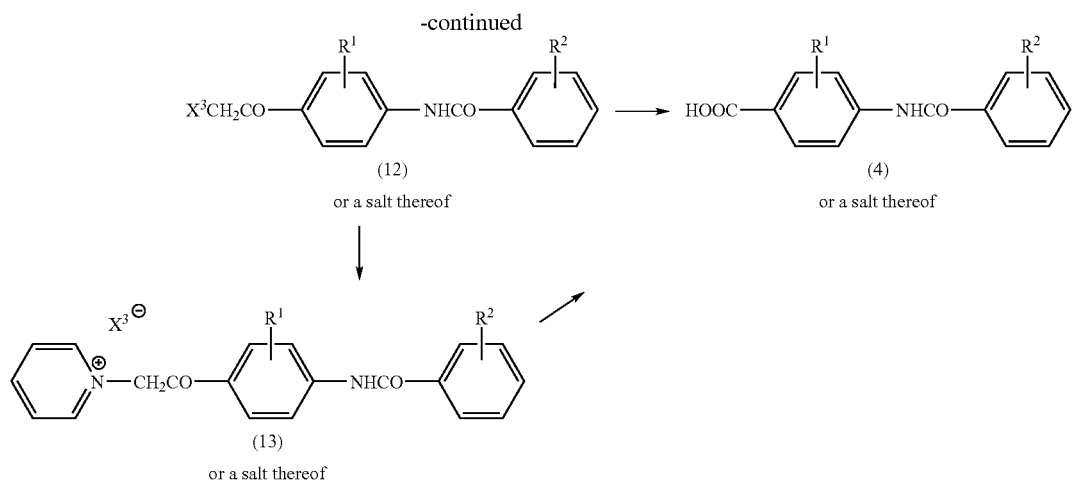

(12)
or a salt thereof (4)
or a salt thereof

(13)
or a salt thereof wherein $R^1$, $R^2$ and $X^3$ are as defined above, $X^4$, $X^5$, $X^6$ and $X^7$ are a halogen atom, and $R^7$ is a lower alkanoyl group.

The halogen atom for $X^4$, $X^5$, $X^6$ and $X^7$ includes fluorine atom, chlorine atom, bromine atom and iodine atom.

The lower alkanoyl group for $R^7$ includes a straight chain or branched chain alkanoyl group having 1 to 6 carbon atoms, for example, formyl, acetyl, propionyl, butyryl, isobutyryl, pentanoyl, tert-butylcarbonyl, or hexanoyl group. Preferred $R^7$ group is acetyl.

The reaction of the amine compound (16) or a salt thereof with the carboxylic acid compound (17) or a salt thereof is carried out by a conventional amido-bond forming reaction. The amido-bond forming reaction can be carried out under the conditions for the conventional amido-bond forming reaction, for example, (a) a mixed acid anhydride process, i.e. a process of reacting the carboxylic acid compound (17) or a salt thereof with an alkyl halocarboxylate to form a mixed acid anhydride and reacting the resultant with the amine compound (16) or a salt thereof; (b) an activated ester process, i.e. a process of converting the carboxylic acid compound (17) or a salt thereof into an activated ester such as p-nitrophenyl ester, N-hydroxysuccinimide ester, 1-hydroxybenzotriazole ester, etc., or into an active amide with benzoxazoline-2-thione, and reacting the resultant with the amine compound (16) or a salt thereof; (c) a carbodiimide process, i.e. a process of condensing the carboxylic acid compound (17) or a salt thereof and the amine compound (16) or a salt thereof in the presence of an activating agent such as dicyclohexylcarbodiimide, 1-(3-dimethylaminopropyl)-3-ethylcarbodiimide (WSC), carbonyldiimidazole, etc.; (d) other processes, i.e. a process of converting the carboxylic acid compound (17) or a salt thereof into a carboxylic anhydride by treating it with a dehydrating agent such as acetic anhydride, and reacting the resultant with the amine compound (16) or a salt thereof; a process of reacting an ester of the carboxylic acid compound (17) or a salt thereof with a lower alcohol and the amine compound (16) or a salt thereof at a high temperature under high pressure; a process of reacting an acid halide compound of the carboxylic acid compound (17) or a salt thereof, i.e. a carboxylic acid halide, with the amine compound (16) or a salt thereof, and the like.

The mixed acid anhydride used in the above mixed acid anhydride process (a) is obtained by the known Schötten-Baumann reaction, and the reaction product is used without isolating from the reaction mixture for the reaction with the amine compound (16) or a salt thereof to give the compound (11) or a salt thereof.

The above Schötten-Baumann reaction is usually carried out in the presence of a basic compound.

The basic compound is any conventional compounds used in the Schötten-Baumann reaction and includes, for example, organic bases such as triethylamine, trimethylamine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), and inorganic bases such as carbonates (e.g. sodium carbonate, potassium carbonate, sodium hydrogen carbonate, potassium hydrogen carbonate), metal hydroxides (e.g. sodium hydroxide, potassium hydroxide, calcium hydroxide), hydrides (e.g. potassium hydride, sodium hydride), alkali metals (e.g. potassium, sodium), amide salts (sodium amide, potassium amide), metal alcoholates (sodium methylate, sodium ethylate). These basic compounds may be used alone or in a mixture of two or more thereof.

The reaction is usually carried out at a temperature of −20° C. to 100° C., preferably −10° C. to 50° C., and the reaction time is usually in the range of about 5 minutes to about 10 hours, preferably about 5 minutes to about 2 hours.

The reaction of the mixed acid anhydride thus obtained with the amine compound (16) or a salt thereof is usually carried out at a temperature of −20° C. to 150° C., preferably −10° C. to 50° C., and the reaction time is usually in the range of about 5 minutes to about 10 hours, preferably about 5 minutes to about 5 hours.

The mixed acid anhydride process is usually carried out in a solvent. The solvent may be any conventional solvents which are usually used in the mixed acid anhydride process and includes, for example, halogenated hydrocarbons (e.g. chloroform, dichloromethane, dichloroethane, carbon tetrachloride, etc.), aromatic hydrocarbons (e.g. benzene, toluene, xylene, etc.), ethers (e.g. diethyl ether, diisopropyl ether, tetrahydrofuran, dimethoxyethane, etc.), esters (e.g. methyl acetate, ethyl acetate, isopropyl acetate, butyl acetate, etc.), aprotic polar solvents (e.g. N,N-dimethylformamide, hexamethylphosphoric triamide, etc.), or a mixture thereof.

The alkyl halocarboxylate used in the mixed acid anhydride process includes, for example, methyl chloroformate, methyl bromoformate, ethyl chloroformate, ethyl bromoformate, isobutyl chloroformate, and the like.

In the mixed acid anhydride process, the carboxylic acid compound (17) or a salt thereof, the alkyl halocarboxylate and the amine compound (16) or a salt thereof are usually used in each equimolar amount, but preferably the alkyl halocarboxylate and the carboxylic acid compound (17) or a salt thereof are used each in an amount of about 1 to 1.5 mole per 1 mole of the amine compound (16) or a salt thereof.

The process of condensing the carboxylic acid compound (17) or a salt thereof and the amine compound (16) or a salt thereof in the presence of an activating agent is carried out in an appropriate solvent in the presence or absence of a basic compound. The solvent and basic compound to be used in this process are the same as those which are used in the process of reacting a carboxylic halide and the amine compound (16) in other processes (d). The activating agent is usually used at least in an equimolar amount, preferably in an amount of about 1 to 5 moles, to 1 mole of the compound (16) or a salt thereof. When WSC is used as the activating agent, the reaction can proceed advantageously by adding 1-hydroxybenzotriazole and/or an acid (e.g. hydrochloric acid) to the reaction system. The reaction is usually carried out at a temperature of −20° C. to 180° C., preferably −10° C. to 150° C., and the reaction time is usually in the range of about 5 minutes to about 90 hours.

Among the other processes (d), when the process of reacting the amine compound (16) or a salt thereof with a carboxylic acid halide is used, the reaction is usually carried out in an appropriate solvent in the presence of a basic compound. The basic compound is any conventional compounds used in the Schötten-Baumann reaction as mentioned above. The solvent includes, in addition to the solvents used in the above mixed acid anhydride process, alcohols (e.g. methanol, ethanol, isopropanol, propanol, butanol, 3-methoxy-1-butanol, ethyl cellosolve, methyl cellosolve, etc.), acetonitrile, pyridine, acetone, water, N-methylpyrrolidone, and the like. These solvents may be used alone or in a mixture of two or more thereof. The ratio of the amounts of the amine compound (16) or a salt thereof and the carboxylic acid halide is not specified, but the amine compound (16) or a salt thereof is usually used at least in an equimolar amount, preferably in an amount of about 1 to 5 moles, to 1 mole of the carboxylic acid halide. The reaction is usually carried out at a temperature of −20° C. to 180° C., preferably −10° C. to 150° C., and the reaction time is usually in the range of about 5 minutes to about 50 hours.

The amido-bond forming reaction in the above Reaction Scheme-V may also be carried out by reacting the carboxylic acid compound (17) or a salt thereof and the amine compound (16) or a salt thereof in the presence of a condensing agent such as phosphorus compounds (e.g. diphenylphosphinyl chloride, phenyl-N-phenylphosphoramide chloridate, diethyl chlorophosphate, diethyl cyanophosphate, diphenylphosphoric azide, bis(2-oxo-3-oxazolidinyl)phosphinic chloride, etc.). These condensing agents may be used alone or in a mixture of two or more thereof. The reaction may be carried out in a solvent in the presence of a basic compound as used in the above reaction of the carboxylic acid halide and the amine compound (16) or a salt thereof at a temperature of −20° C. to 150° C., preferably −10° C. to 100° C., for about 5 minutes to about 30 hours. The condensing agent and the carboxylic acid compound (17) or a salt thereof are each used at least in an equimolar amount, preferably in an amount of about 1 to 2 moles, to 1 mole of the amine compound (16) or a salt thereof.

In the above Reaction Scheme-V, the reaction of the compound (11) or a salt thereof and the compound (15a) or (15b) to give the compound (14) or a salt thereof is so-called Friedel-Crafts reaction, which is carried out in an appropriate solvent in the presence of Lewis acid.

The Lewis acid may be any conventional Lewis acids which are usually used in Friedel-Crafts reaction, and includes, for example, aluminum chloride, zinc chloride, ferric chloride, stannic chloride, boron tribromide, titanium tetrachloride, conc. sulfuric acid, methanesulfonic acid, and the like. These Lewis acids may be used alone or in a mixture of two or more thereof. The Lewis acids are usually used in an amount of about 1 to 6 moles per 1 mole of the compound (11) or a salt thereof.

The solvent to be used in said reaction includes, for example, carbon disulfide, nitromethane, aromatic hydrocarbons (e.g. nitrobenzene, chlorobenzene, o-dichlorobenzene, etc.), halogenated hydrocarbons (e.g. dichloromethane, dichloroethane, carbon tetrachloride, tetrachloroethane, etc.), or a mixture thereof.

The compound (15a) or (15b) is used at least in an equimolar amount, preferably in an amount of about 1 to 5 moles, to 1 mole of the compound (11) or a salt thereof. The reaction is usually carried out at a temperature of 0° C. to 120° C., preferably 0° C. to 70° C., for about 0.5 to about 24 hours.

The conversion reaction of the compound (14) or a salt thereof into the compound (4) or a salt thereof is carried out in an appropriate solvent in the presence of an oxidizing agent.

The solvent includes, for example, water, alcohols (e.g. methanol, ethanol, propanol, isopropyl alcohol n-butanol, tert-butanol, ethylene glycol, etc.), halogenated hydrocarbons (e.g. dichloromethane, chloroform, carbon tetrachloride, etc.), ethers (e.g. diethyl ether, tetrahydrofuran, dioxane, monoglyme, diglyme, etc.), ketones (e.g. acetone, methyl ethyl ketone, etc.), aromatic hydrocarbons (e.g. benzene, o-dichlorobenzene, toluene, xylene, etc.), esters (e.g. methyl acetate, ethyl acetate, etc.), aprotic polar solvents (e.g. acetonitrile, N,N-dimethylformamide, hexamethylphosphoric triamide, etc.), or a mixture thereof.

The oxidizing agent includes hypohalogenous acids (e.g. hypochlorous acid, hypoiodous acid, hypobromous acid, etc.), alkali metal or alkaline earth metal hypohalites (e.g. sodium hypochlorite, sodium hypoiodite, sodium hypobromite, potassium hypochlorite, calcium hypochlorite, potassium hypoiodite, potassium hypobromite, etc.), alkali metal permanganates (e.g. potassium permanganate, etc.), chromic acids or alkali metal salts thereof (e.g. chromium (VI) oxide, sodium dichromate, potassium dichromate, etc.), nitric acid, and the like. When alkali metal permanganates are used, it is preferable to carry out the reaction in the presence of an inorganic base such as potassium hydroxide, sodium hydroxide, sodium carbonate, or potassium carbonate. When chromic acid or an alkali metal salt thereof is used, it is preferable to carry out the reaction in the presence of a mineral acid (e.g. sulfuric acid, etc.) or an organic acid (e.g. acetic acid, etc.). Among the above oxidizing agents, hypohalogenous acids, alkali metal hypohalites are particularly suitable.

The oxidizing agent is used at least in an equimolar amount, preferably in an amount of about 1 to 10 moles, to 1 mole of the compound (14) or a salt thereof. The reaction is usually carried out at a temperature of −20° C. to 50° C., preferably −20° C. to around room temperature, for about 1 to about 30 hours.

The reaction of the compound (11) or a salt thereof with the compound (18a) or (18b) to give the compound (12) or a salt thereof is carried out under the same conditions as in the reaction of the compound (11) or a salt thereof with the compound (15a) or (15b) to give the compound (14) or a salt thereof.

The reaction of converting the compound (12) or a salt thereof into the compound (13) or a salt thereof is carried out by reacting it with pyridine in an appropriate solvent. The solvent includes any solvents to be used in the above process for preparing the compound (1) or a salt thereof.

The reaction is usually carried out at a temperature of 0° C. to about 150° C., preferably room temperature to about 100° C., for about 1 to about 10 hours. Pyridine is used at least in an equimolar amount, preferably in an amount of about 1 to 5 moles, to 1 mole of the compound (12) or a salt thereof.

The above reaction for producing the compound (13) or a salt thereof may also be carried out by reacting the reaction mixture, which is obtained in the reaction of the compound (11) or a salt thereof with the compound (18a) or (18b) to give the compound (12) or a salt thereof, with pyridine without isolating the produced compound (12) or a salt thereof under the same conditions as above.

The reaction of converting the compound (13) or a salt thereof into the compound (4) or a salt thereof is carried out by hydrolyzing it. The hydrolyzing reaction is carried out in an appropriate solvent or without solvent in the presence of a basic compound.

The solvent includes, for example, water, alcohols (e.g. methanol, ethanol, propanol, isopropylalcohol, tert-butanol, etc.), ketones (e.g. acetone, methyl ethyl ketone, etc.), ethers (e.g. diethyl ether, dioxane, tetrahydrofuran, monoglyme, diglyme, etc.), aliphatic acids (e.g. acetic acid, formic acid, etc.), esters (e.g. methyl acetate, ethyl acetate, etc.), halogenated hydrocarbons (e.g. chloroform, dichloromethane, dichloroethane, carbon tetrachloride, etc.), aprotic polar solvents (e.g. N,N-dimethylformamide, hexamethylphosphoric triamide, etc.), or a mixture thereof.

The basic compound includes carbonates (e.g. sodium carbonate, potassium carbonate, sodium hydrogen carbonate, potassium hydrogen carbonate, etc.), metal hydroxides (e.g. sodium hydroxide, potassium hydroxide, calcium hydroxide, lithium hydroxide, etc.), and the like. These basic compounds may be used alone or a mixture of two or more thereof.

The hydrolyzing reaction is usually carried out at a temperature of 0° C. to about 200° C., preferably 0° C. to about 150° C., for about 10 minutes to about 30 hours. The basic compound is usually used at least in an equimolar amount, preferably in an amount of about 1 to 5 moles, to 1 mole of the compound (13) or a salt thereof.

The reaction of the compound (11) or a salt thereof with the compound (19) to give the compound (4) or a salt thereof is carried out under the same conditions as in the reaction of the compound (11) or a salt thereof with the compound (15a) or (15b) to give the compound (14) or a salt thereof.

The reaction of converting the compound (12) or a salt thereof into the compound (4) or a salt thereof is carried out under the same conditions as in the reaction of converting the compound (14) or a salt thereof into the compound (4) or a salt thereof.

The reaction of the compound (16) or a salt thereof with the compound (20) or a salt thereof is carried out under the same conditions as in the reaction of the compound (16) or a salt thereof with the compound (17) or a salt thereof.

The reaction of the compound (21) or a salt thereof with the compound (15a) or (15b) is carried out under the same conditions as in the reaction of the compound (11) or a salt thereof with the compound (15a) or (15b).

The reaction of converting the compound (22) or a salt thereof into the compound (23) or a salt thereof is carried out under the same conditions as in the reaction of converting the compound (14) or a salt thereof into the compound (4) or a salt thereof.

The reaction of converting the compound (23) or a salt thereof into the compound (24) or a salt thereof is carried out under the same conditions as in the reaction of converting the compound (13) or a salt thereof into the compound (4) or a salt thereof.

The reaction of the compound (24) or a salt thereof with the compound (17) or a salt thereof is carried out under the same conditions as in the reaction of the compound (16) or a salt thereof with the compound (17) or a salt thereof.

After the reaction, the produced compound (11) or a salt thereof, compound (12) or a salt thereof, compound (13) or a salt thereof, compound (14) or a salt thereof, compound (4) or a salt thereof, compound (21) or a salt thereof, compound (22) or a salt thereof, compound (23) or a salt thereof, compound (24) or a salt thereof may be isolated from the reaction mixture, for example, by cooling the reaction mixture, followed by conventional isolation methods, such as filtration, concentration, extraction. Further, those compound (11) or a salt thereof, compound (12) or a salt thereof, compound (13) or a salt thereof, compound (14) or a salt thereof, compound (4) or a salt thereof, compound (21) or a salt thereof, compound (22) or a salt thereof, compound (23) or a salt thereof, compound (24) or a salt thereof may be purified from the reaction mixture by conventional purification methods such as column chromatography, recrystallization. The recrystallization may be done by using a seed crystal, or alternatively may be done with active carbon.

Where the compound (4) is produced by the reaction as shown in Reaction Scheme-V, it can be converted into a salt of the compound (4) by treating it with a pharmaceutically acceptable acidic compound or a basic compound. The acidic compound includes, for example, an inorganic acid (e.g. hydrochloric acid, hydrobromic acid, nitric acid, sulfuric acid, phosphoric acid), an organic acid (e.g. methanesulfonic acid, ethanesulfonic acid, p-toluenesulfonic acid, acetic acid, citric acid, tartaric acid, oxalic acid, maleic acid, fumaric acid, malic acid, succinic acid, benzoic acid). The basic compound includes, for example, sodium hydroxide, potassium hydroxide, lithium hydroxide, calcium hydroxide, sodium carbonate, potassium carbonate, sodium hydrogen carbonate, potassium hydrogen carbonate.

INDUSTRIAL APPLICABILITY

The desired compounds (1) or a salt thereof and the intermediate compounds (4) or a salt thereof of the present invention, which are useful for preparing a pharmaceutically active 2,3,4,5-tetrahydro-1H-1-benzazepine compound having vasopressin antagonistic activity, can be produced by the reactions as described above in high yield and high purity. Moreover, according to the process of the present invention, the compound (10) or a salt thereof can be obtained in a high yield and high purity.

Particularly, according to the process of the present invention, the compound (4) or a salt thereof can be obtained in a high yield and high purity without taking complicated purification steps and further the starting materials to be used for the production thereof such as the compound (16) or a salt thereof, the compound (17) or a salt thereof, and further the compounds (15a), (15b), (18a), (18b), (19) and (20) are all commercially available in high purity, and hence, by utilizing the process for production of the compound (4) or a salt thereof of the present invention, the desired compound (1) or a salt thereof can be advantageously obtained on an industrial scale even by the known method as shown in Reaction Scheme A.

Besides, the starting compounds (7) and (8) to be used for the production of the compound (1) or a salt thereof as shown in Reaction Schemes II and III are publicly available and can be commercially obtained in a high purity. Further, the methods of the present invention can be carried out without many reacting agents and hence the compounds (1), (4) and (10) or their salts can be obtained with a lower cost than in the known methods. Thus, the methods of the present invention are suitable for the production of the compounds (1), (4) and (10) and their salts on industrial scale.

BEST MODE FOR CARRYING OUT THE INVENTION

The present invention is illustrated in more detail by the following Reference Examples and Examples but should not be construed to be limited thereof.

Reference Example 1

Preparation of 7-chloro-2,3,4,5-tetrahydro-1H-1-benzazepin-5-one

7-Chloro-1-p-toluenesulfonyl-2,3,4,5-tetrahydro-1H-1-benzazepin-5-one (5 g) is added to 90% (w/w) sulfuric acid (50 ml), and the mixture is stirred at 0° C. to 10° C. for 2.5 hours. The reaction mixture is added to a cool water (50 mL) and then is neutralized by gradually adding thereto a solution of sodium hydroxide (75 g) in an appropriate amount of water with attention to exothermal reaction. The reaction mixture is cooled to 25° C., and the resulting yellowish green suspension is extracted with toluene (50 mL), and the organic layer is separated, washed with water (25 ml×2) and dried over sodium sulfate. After filtering off sodium sulfate, the filtrate is concentrated under reduced pressure to give a pale yellow crystals. The crystals are subjected to azeotropic dehydration with toluene in order to remove a slight amount of water to give 7-chloro-2,3,4,5-tetrahydro-1H-1-benzazepin-5-one having a moisture content of less than 100 ppm (2.5 g, yield 89%, M.p. 103-104° C.).

The 7-chloro-2,3,4,5-tetrahydro-1H-1-benzazepin-5-one is further recrystallized from methanol/water (7:3) to give pale yellow needles.

The 7-chloro-2,3,4,5-tetrahydro-1H-1-benzazepin-5-one thus obtained has the following physical data; (1) NMR spectrum data, (2) IR spectrum data, (3) MS spectrum data.
(1) NMR Spectrum:
$^1$H NMR (300 MHz, CDCl$_3$): δ=2.18 (tt, J=7.1 Hz, J=6.6 Hz, 2H), 2.82 (t, J=7.1 Hz, 2H), 3.25 (td, J=6.6 Hz, J=4.6 Hz, 2H), 4.62 (br s, 1H), 6.69 (d, J=8.7 Hz, 1H), 7.17 (dd, J=8.7 Hz, J=2.5 Hz, 1H), 7.68 (d, J=2.5 Hz, 1H)
(2) IR Spectrum
IR (KBr): 3365, 2963, 2933, 1655, 1607, 1287, 842, 820 cm$^{-1}$
(3) MS Spectrum
MS (EI): m/z=195 (M$^+$).

Reference Example 2

Preparation of 2-bromo-5-(2-methylbenzoylamino)toluene 3-(2-methylbenzoylamino)toluene (80 g) is dissolved in acetic acid (500 mL), and thereto is added a solution of bromine (19.0 ml) in acetic acid (40 mL) with stirring under ice cooling over a period of about one hour. During which the mixture is cooled at an inner temperature of below 20° C. (mean inner temperature: 10-15° C.) since the temperature raises. The reaction mixture is continuously stirred overnight. The resulting suspension is added to ice-water, and the resulting crystals are taken by filtration, washed with water, and dried at 60° C. The resultant is recrystallized from methanol-water to give 2-bromo-5-(2-methylbenzoylamino)toluene (105.0 g), white needles (yield 97%, Mp 144.5-146.0° C.)

The 2-bromo-5-(2-methylbenzoylamino)toluene thus obtained has the following NMR spectrum:
$^1$H NMR (300 MHz, CDCl$_3$): δ=2.39 (s, 3H), 2.48 (s, 3H), 7.24-7.56 (m, 8H).

Reference Example 3

Preparation of 3-(2-methylbenzoylamino)toluene m-Toluidine (1772 g) is dissolved in acetone (3.5 L), and thereto is added a solution of sodium hydroxide (648 g) in water (6.25 L), and the mixture is cooled to around 20° C. To the mixture is added o-methylbenzoyl chloride (2507 g) over a period of about 20 minutes with stirring, by which the temperature of the reaction mixture raises to around 60° C. After stirring for about one hour, the reaction mixture is cooled around 10° C. and the resulting crystals are taken by filtration. The crystalline product is washed 2 times with methanol/water (4:1, 3.75 L), and dried at about 60° C. to give the desired product (3530 g, yield 96.62%).
$^1$H NMR (300 MHz, CDCl$_3$): δ=2.37 (3H, s), 2.50 (3H, s), 6.96 (1H, br.d, J=7.2 Hz), 7.20-7.29 (3H, m), 7.35 (2H, br.t, J=7.4 Hz), 7.43-7.52 (3H, m)
m.p. 144.8-145.8° C., colorless prisms Reference Example 4

Preparation of 2-methyl-4-(2-methylbenzoylamino)acetophenone 3-(2-Methylbenzoylamino)toluene (1500 g) is suspended in o-dichlorobenzene (4.5 L), and the mixture is cooled to around 5° C., and thereto is added portionwise aluminum chloride (3556 g) (the temperature of the reaction mixture raises to 35° C.). The mixture is again cooled to around 5° C., and thereto is added acetyl chloride (571 mL) portionwise at an interval of 20 minutes in each amount of ¼ volume thereof. Thereafter, the mixture is continuously stirred for about 5 hours at around 10° C. to complete the reaction. The resulting reaction mixture is slowly added to a vessel containing ice (15 kg) with attention to exothermic reaction and fuming. The organic layer is separated and washed twice with 5% aqueous sodium hydrogen carbonate solution (7.5 L) which is previously heated to 50° C. The organic layer thus obtained is heated to 40° C. and thereto are added methanol (0.75 L) and 5% aqueous sodium hydroxide solution (675 mL). After stirring, the organic layer is separated and washed three times with water (4.5 L, around 50° C.) and then cooled to around 5° C. The resultant is continuously cooled for about 3 hours, and the resultant crystals are separated by filtration, and dried at around 60° C. to give the desired compound (1189 g, yield 66.8%).
$^1$H NMR (300 MHz, CDCl$_3$): δ=2.50 (3H, s), 2.56 (6H, s), 7.25 (1H, br.t, J=7.2 Hz), 7.27 (1H, d, J=7.1 Hz), 7.37 (1H, br.t, J=7.3 Hz), 7.43 (1H, br.s), 7.47 (1H, br.d, J=7.1 Hz), 7.65, (1H, br.d, J=8.1 Hz), 7.72 (1H, br.s), 7.76 (1H, d, J=8.1 Hz)
M.p. 101.3-102.1° C., colorless prisms Reference Example 5

Preparation of 2-chloro-2'-methyl-4'-(2-methylbenzoylamino)acetophenone and 2-chloro-4'-methyl-2'-(2-methylbenzoylamino)acetophenone 3-(2-Methylbenzoylamino)toluene (136.5 g) is suspended in nitroethane (137 mL), and thereto is slowly added aluminum chloride (403.9 g) under ice cooling so as to do not exceed 60° C. The mixture is cooled to below 20° C., and thereto is added chloroacetyl chloride (136.8 g), and the mixture is stirred at around 20° C. for about 7.5 hours to complete the reaction. To the reaction mixture is slowly added ice water (1.36 L) so as to do not exceed 50° C., and then extracted with toluene (0.68 L). The toluene layer is washed with saturated aqueous sodium hydrogen carbonate solution (0.68 L) and saturated saline solution (0.68 L) in this order. A part of the resulting toluene solution is separated and subjected to the following procedure, while the remaining parts of the toluene solution are used in the procedure in Reference Example 6.

A part of the toluene solution thus separated is concentrated to dryness under reduced pressure to give a mixture of 2-chloro-2'-methyl-4'-(2-methylbenzoylamino)acetophenone and 2-chloro-4'-methyl-2'-(2-methylbenzoylamino)acetophenone having the following NMR spectrum.

$^1$H NMR (300 MHz, CDCl$_3$): δ=2.50 (3H, s), 2.57 (3H, s), 4.64 (2H, s), 7.26 (1H, br.t, J=7.6 Hz), 7.28 (1H, d, J=7.6 Hz), 7.38 (1H, br.t, J=7.5 Hz), 7.48 (1H, br.d, J=7.8 Hz), 7.49 (1H, br.s), 7.68, (1H, br.d, J=9 Hz), 7.70 (1H, br.s), 7.72 (1H, d, J=9 Hz)

Reference Example 6

Preparation of a mixture of 1-{2-[2-methyl-4-(2-methylbenzoylamino)phenyl]-2-oxoethyl}pyridinium chloride and 1-{2-[4-methyl-2-(2-methylbenzoylamino)phenyl]-2-oxoethyl}pyridinium chloride To the toluene solution obtained in the above Reference Example 5 is added pyridine (143.8 g) and the mixture is stirred at 60-78° C. for about 4.5 hours to complete the reaction. The reaction mixture is stirred under ice cooling for about one hour, and the resulting crystals are separated by filtration. The resulting crystals are washed with toluene and dried at around 60° C. to give the desired product mixture (207.3 g, yield 89.8%).

$^1$H NMR (300 MHz, DMSO-d$_6$): δ=2.41 (3H, s), 2.50 (3H, s), 6.45 (2H, s), 7.33 (1H, br.t, J=7 Hz), 7.34 (1H, d, J=7.5 Hz), 7.44 (1H, br.t, J=7.5 Hz), 7.51 (1H, br.d, J=7.5 Hz), 7.81 (1H, br.s), 7.89 (1H, br.d, J=8.1 Hz), 8.12 (1H, d, J=8.1 Hz), 8.28 (2H, dd, J=6.6, 7.5 Hz), 8.74 (1H, br.t, J=7.5 Hz), 9.06 (2H, br.d, J=6.6 Hz), 10.75 (1H, br.s)

Example 1

Preparation of 7-chloro-1-[2-methyl-4-(2-methylbenzoylamino)benzoyl]-2,3,4,5-tetrahydro-1H-1-benzazepin-5-one Well-dried 2-bromo-5-(2-methylbenzoylamino)toluene (3.2 g, 10.5 mM) and 7-chloro-2,3,4,5-tetrahydro-1H-1-benzazepin-5-one (1.8 g, 9.2 mM) are entered into a reaction vessel, and thereto are added 1,8-diazabicyclo[5.4.0]undecene-7 (DBU) (2.5 mL) and N,N-dimethylformamide (DMF) (6 mL), and the mixture is stirred at room temperature. To the solution thus obtained are added triphenylphosphine (221 mg) and Pd(OAc)$_2$ (23.5 mg, 0.105 mM), and the mixture is heated under carbon monoxide at 125° C. for 3 hours. The reaction mixture is cooled till room temperature, and thereto is blown argon gas to discharge excess carbon monoxide. Thereafter, to the mixture are added ethyl acetate (150 mL) and 0.5M aqueous NaOH solution (50 mL) to divide into two phases. The organic layer is washed with diluted hydrochloric acid and then with saturated saline and dried over magnesium sulfate. After filtering off magnesium sulfate, the filtrate is concentrated under reduced pressure, and the residue is purified by silica gel column chromatography (eluent: ethyl acetate/n-hexane) to give the desired 7-chloro-1-[2-methyl-4-(2-methylbenzoylamino)benzoyl]-2,3,4,5-tetrahydro-1H-1-benzazepin-5-one (3.5 g) as pale yellowish white crystalline powder (Yield 85%, purity 99.1%, Mp 134-142° C.).

The 7-chloro-1-[2-methyl-4-(2-methylbenzoylamino)benzoyl]-2,3,4,5-tetrahydro-1H-1-benzazepin-5-one thus obtained has the following physical data; (1) NMR spectrum data, (2) IR spectrum data, (3) MS spectrum data.

(1) NMR Spectrum:

$^1$H NMR (300 MHz, DMSO-d$_6$, 100° C.): δ=1.98 (tt, J=6.6 Hz, J=6.6 Hz, 2H), 2.29 (s, 3H), 2.36 (s, 3H), 2.78 (t, J=6.4 Hz, 2H), 3.87 (t, J=6.4 Hz, 2H), 6.96 (d, J=8.5 Hz, 1H), 7.09 (d, J=8.5 Hz, 1H), 7.24 (m, 2H), 7.32-7.46 (m, 4H), 7.59 (m, 2H), 9.96 (brs, 1H)

(2) IR Spectrum

IR (KBr): 3296, 2964, 2926, 1683, 1638, 1610, 1401, 1297, 836, 739 cm$^{-1}$ (3) MS Spectrum MS (EI): m/z=446 (M$^+$).

The purity is measured by high performance liquid chromatography (HPLC) under the following conditions:

Detector: Ultraviolet absorptiometer (UV 254 nm), column: YMC-Pack ODS-AA-312, column temperature: around 25° C., mobile phase: acetonitrile/water/phosphoric acid solution (700:300:1).

Example 2

Preparation of 7-chloro-5-hydroxy-1-[2-methyl-4-(2-methylbenzoylamino)benzoyl]-2,3,4,5-tetrahydro-1H-1-benzazepine 7-Chloro-1-[2-methyl-4-(2-methylbenzoylamino)benzoyl]-2,3,4,5-tetrahydro-1H-1-benzazepin-5-one (3.2 g, 7.1 mM) is suspended in methanol (27 mL), and thereto is added at one time crystalline sodium borohydride (96 mg=2.5 mM), and the mixture is reacted for about one hours. To the reaction mixture is added dropwise 0.5% diluted hydrochloric acid (9.3 mL), and the mixture is stirred at room temperature and then cooled. The precipitated crystals are separated by filtration, and dried at room temperature to give the desired 7-chloro-5-hydroxy-1-[2-methyl-4-(2-methylbenzoylamino)benzoyl]-2,3,4,5-tetrahydro-1H-1-benzazepine (2.97 g) as white powder (Yield 92%, Mp 224.5-225.5° C.).

The pure 7-chloro-5-hydroxy-1-[2-methyl-4-(2-methylbenzoylamino)benzoyl]-2,3,4,5-tetrahydro-1H-1-benzazepine is obtained by recrystallizing the above product from methanol/water (4:1). The product thus obtained is while crystalline powder (yield of recrystallization, 90%, purity more than 99.5%, Mp 226-227.5° C.).

The 7-chloro-5-hydroxy-1-[2-methyl-4-(2-methylbenzoylamino)benzoyl]-2,3,4,5-tetrahydro-1H-1-benzazepine thus obtained has the following physical data; (1) NMR spectrum data, (2) IR spectrum data, (3) MS spectrum data and (4) powder X-ray diffraction spectrum data.

(1) NMR Spectrum:

$^1$H NMR (300 MHz, DMSO-$d_6$): major conformational isomer δ=1.49 (br ddd, J=11.3 Hz, J=11.3 Hz, J=11.3 Hz, 1H), 1.74 (br d, J=11.3 Hz, 1H), 1.95 (br ddd, J=11.3 Hz, J=11.3 Hz, J=11.3 Hz, 1H), 2.11 (br d, J=11.3 Hz, 1H), 2.34 (s, 6H), 2.68 (br dd, J=11.3 Hz, J=11.3 Hz, 1H), 4.64 (br d, J=11.3 Hz, 1H), 4.90 (br d, J=11.3 Hz, 1H), 5.70 (br d, J=4.6 Hz, 1H), 6.74 (d, J=8.2 Hz, 1H), 6.76 (d, J=10.1 Hz, 1H), 7.05 (dd, J=8.2 Hz, J=2.3 Hz, 1H), 7.25-7.29 (m, 3H), 7.37 (dd, J=7.3 Hz, J=7.3 Hz, 1H), 7.41 (d, J=7.3 Hz, 1H), 7.50 (d, J=2.3 Hz, 1H), 7.60 (s, 1H), 10.2 (s, 1H)

(2) IR Spectrum

IR (KBr): 3397, 3221, 2926, 1657, 1622, 1609, 1395, 1304, 1094, 866, 827, 745 cm$^{-1}$ (3) MS Spectrum MS (FAB): m/z=449 (MH$^+$)

(4) Powder X-Ray Diffraction Spectrum

2θ=4.7, 15.4, 18.7, 21.7, 23.5°.

The purity is measured by high performance liquid chromatography (HPLC) under the following conditions:

Detector: Ultraviolet absorptiometer (UV 254 nm), column: YMC-Pack ODS-A A-312, column temperature: around 25° C., mobile phase: acetonitrile/water/phosphoric acid solution (500:500:1) or acetonitrile/water/phosphoric acid solution (700:300:1).

In the above procedure, the following compounds (A), (B), (C) and (D) or their salts are occasionally obtained in an amount of 0.01 to 0.03% by weight respectively in addition to the above 7-chloro-5-hydroxy-1-[2-methyl-4-(2-methylbenzoylamino)benzoyl]-2,3,4,5-tetrahydro-1H-1-benzazepine or a salt thereof. These compounds can be easily separated in the same manner as in the separation of the compound (10) or a salt thereof as mentioned above. These compounds also exhibit vasopressin antagonistic activity and are useful as a vasopressin antagonist.

Compound (A)

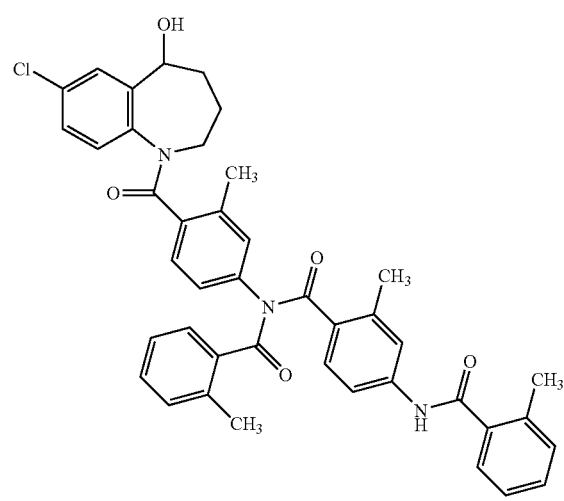

Compound (B)

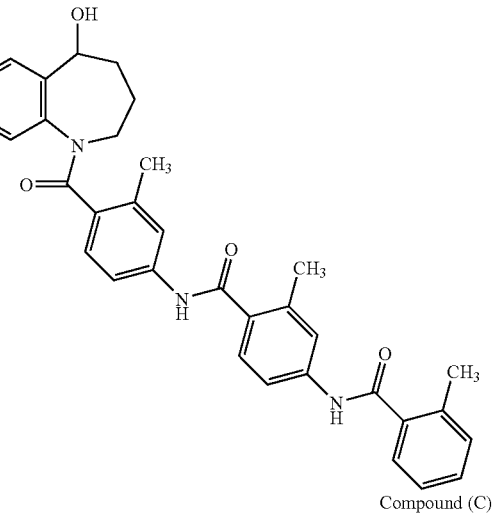

Compound (C)

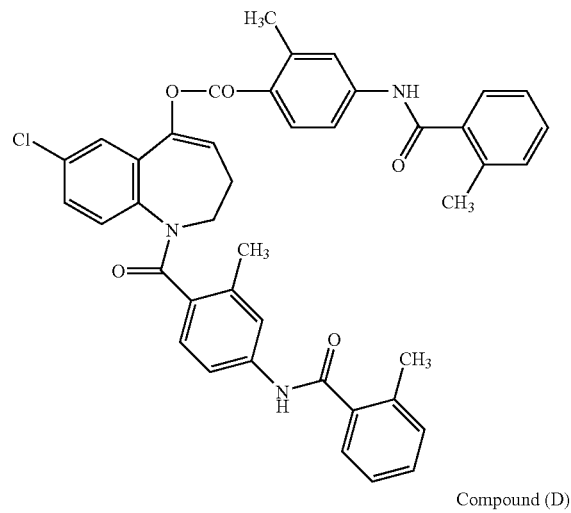

Compound (D)

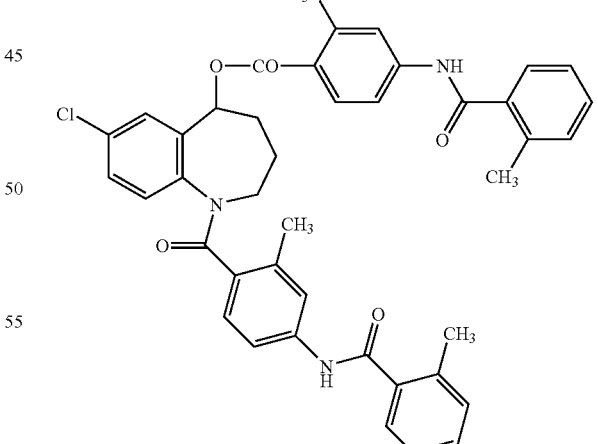

The NMR Spectrum of Compound (A):

$^1$H NMR (300 MHz, DMSO-$d_6$): δ=1.49 (1H, m), 1.75 (1H, br), 1.93 (1H, m), 2.10 (1H, m), 2.27 (3H, s), 2.30 (3H, s), 2.36 (6H, s), 2.68 (1H, t, J=12 Hz), 4.60 (1H, m), 4.85 (1H, m), 5.69 (1H, m), 6.59 (1H, d, J=8.4 Hz), 6.78 (1H, m), 6.88 (1H, dd, J=8.4 Hz, J=2.7 Hz), 6.91 (1H, m), 7.10 (1H, m), 7.15 (1H, m), 7.20 (1H, m), 7.29 (1H, m), 7.31 (2H, m), 7.47 (1H, d, J=2.7 Hz), 7.54 (4H, m), 7.64 (1H, m), 7.68 (1H, m), 10.40 (1H, s)

The NMR Spectrum of Compound (B):

$^1$H NMR (300 MHz, DMSO-$d_6$): δ=1.49 (1H, m), 1.76 (1H, br), 1.93 (1H, m), 2.11 (1H, br), 2.34 (3H, s), 2.35 (3H, s), 2.38 (3H, s), 2.68 (1H, t, J=12 Hz), 4.65 (1H, m), 4.90 (1H, m), 5.70 (1H, d, J=4.5 Hz), 6.74 (1H, d, J=8.1 Hz), 6.76 (1H, d, J=6.0 Hz), 7.05 (1H, dd, J=2.7 Hz, J=8.1 Hz), 7.23-7.50 (7H, m), 7.59-7.73 (3H, m), 10.13 (1H, s), 10.39 (1H, s)

The NMR Spectrum of Compound (C):

$^1$H NMR (300 MHz, DMSO-$d_6$): δ=2.34 (3H, s), 2.39 (3H, s), 2.40 (3H, s), 2.59 (3H, s), 2.66 (1H, m), 2.93 (2H, m), 4.83 (1H, m), 6.26 (1H, m), 6.83 (1H, d, J=8.7 Hz), 7.14 (1H, m), 7.16 (1H, dd, J=8.7 Hz, J=2.3 Hz), 7.27-7.51 (8H, m), 7.28 (1H, m), 7.37 (1H, d, J=2.3 Hz), 7.66 (1H, m), 7.81 (1H, d, J=2.1 Hz), 7.82 (1H, dd, J=2.1 Hz, J=9.4 Hz), 8.24 (1H, d, J=9.4 Hz), 10.25 (1H, s), 10.66 (1H, s)

The NMR Spectrum of Compound (D):

$^1$H NMR (300 MHz, DMSO-$d_6$, 160° C.): δ=1.93 (2H, m), 2.05 (1H, m), 2.16 (1H, m), 2.37 (3H, s), 2.38 (3H, s), 2.40 (3H, s), 2.58 (3H, s), 3.50 (1H, m), 3.94 (1H, m), 6.21 (1H, dd, J=8.4 Hz, J=3.3 Hz), 6.94 (1H, d, J=8.4 Hz), 6.99 (1H, d, J=8.4 Hz), 7.17 (1H, dd, J=8.4 Hz, J=2.7 Hz), 7.21-7.43 (8H, m), 7.28 (1H, dd, J=8.4 Hz, J=1.8 Hz), 7.38 (1H, d, J=2.7 Hz), 7.56 (1H, d, J=1.8 Hz), 7.66 (1H, dd, J=8.4 Hz, J=2.1 Hz), 7.69 (1H, d, J=2.1 Hz), 7.94 (1H, d, J=8.4 Hz), 9.59 (1H, br. s), 9.89 (1H, br. s)

Example 3

Preparation of 2-methyl-4-(2-methylbenzoylamino)benzoic acid

2-Methyl-4-(2-methylbenzoylamino)acetophenone (1000 g, 3.74 mole) is dissolved in isopropyl alcohol (5 L) by heating at 50 to 60° C. The solution is cooled to below 5° C., thereto is added dropwise 12% (w/w) aqueous sodium hypochlorite solution (7665 g, 25.8 mole as an active chlorine (Cl)) with attention not to be over 10° C. (over about 1.5 hour). The mixture is stirred for one hour to complete the reaction. To the reaction mixture is added sodium hydrogen sulfite (187 g, 1.80 mole) and the mixture is stirred for about 30 minutes. To the mixture are added water (4 L) and toluene (5 L), and the mixture is stirred well, and the mixture is allowed to stand to be separated into two layers. To the aqueous layer thus separated is added slowly concentrated hydrochloric acid (1.4 L) and the mixture is cooled to below 20° C., and the precipitated crystals are separated by filtration. The crystals are suspended in water (3 L) to wash them. The product is taken by filtration and dried at 60° C. to give a crude product (1369 g, 135.9%). A part of this crude product (600 g) is recrystallized from methanol (12.6 L) and dried at 60° C. to give the desired product (341 g, yield 77.2%, purity by HPLC 99.8%).

$^1$H NMR (300 MHz, DMSO-$d_6$): δ=2.39 (3H, s), 2.53 (3H, s), 7.31 (br.t, J=7.1 Hz), 7.32 (1H, d, J=7.2 Hz), 7.41 (1H, br.t, J=7.2 Hz), 7.47 (1H, d, J=7.2 Hz), 7.68 (1H, br.d, J=8.2 Hz), 7.69 (1H, s), 7.86 (1H, d, J=8.2 Hz), 10.50 (1H, s), 12.6 (1H, br.s)

M.p. 231.3-232.6° C., white powder

The purity is measured by high performance liquid chromatography (HPLC) under the following conditions:

Detector: Ultraviolet absorptiometer (wavelength, 254 nm), YMC-Pack ODS-A A-312, mobile phase: 3 mmol/L sodium laurylsulfate solution/acetonitrile/phosphoric acid solution 600:400:1), column temperature: at a constant temperature of around 25° C.

Example 4

Preparation of 2-methyl-4-(2-methylbenzoylamino)benzoic acid

The isomer mixture of 1-{2-[2-methyl-4-(2-methylbenzoylamino)phenyl]-2-oxoethyl}pyridinium chloride and 1-{2-[4-methyl-2-(2-methylbenzoylamino)phenyl]-2-oxoethyl}pyridinium chloride obtained in the above Reference Example 6 (207.3 g, 0.544 mole) is suspended in methanol (0.4 L) and thereto is added a solution of sodium hydroxide (52.5 g, 1.31 mole) in water (0.6 L), and the mixture is stirred at 60-76° C. for about 4 hours to complete the reaction. To the reaction mixture is added concentrated hydrochloric acid (0.108 L) at the same temperature to adjust pH=1. The mixture is stirred under ice cooling for one hour, and the precipitated crystals are separated by filtration. The resulting crystals are washed with water and dried at around 60° C. to give the crude product (125.5 g, yield 85.6%). A part of this crude product (20 g) is recrystallized from methanol (340 mL) and dried at 60° C. to give the desired product (12.1 g, yield 60.5%, purity by HPLC 99.7%).

$^1$H NMR (300 MHz, DMSO-$d_6$): δ=2.39 (3H, s), 2.53 (3H, s), 7.31 (br.t, J=7.1 Hz), 7.32 (1H, d, J=7.2 Hz), 7.41 (1H, br.t, J=7.2 Hz), 7.47 (1H, d, J=7.2 Hz), 7.68 (1H, br.d, J=8.2 Hz), 7.69 (1H, s), 7.86 (1H, d, J=8.2 Hz), 10.50 (1H, s), 12.6 (1H, br.s)

M.p. 231.3-232.6° C., while powder

The purity is measured by high performance liquid chromatography (HPLC) under the following conditions:

Detector: Ultraviolet absorptiometer (wavelength, 254 nm), YMC-Pack ODS-A A-312, mobile phase: 3 mmol/L sodium laurylsulfate solution/acetonitrile/phosphoric acid solution 600:400:1), column temperature: at a constant temperature of around 25° C.

Example 5

Preparation of 2-methyl-4-(2-methylbenzoylamino)benzoic acid

To a solution of 3-(2-methylbenzoylamino)toluene (50.0 g, 0.222 mole) in methylene chloride (50 mL) which is cooled to 3° C. is added aluminum chloride (88.8 g, 0.666 mole) under nitrogen atmosphere over a period of about 10 minutes. The mixture is cooled to 3° C., and thereto is added dropwise oxalyl chloride (25.2 mL, 0.289 mole) at 3-7° C. The mixture is stirred at 2-7° C. for 5 hours. After confirming the disappearance of the starting materials, the reaction mixture is diluted with methylene chloride (100 mL), and thereto is added ice water to quench the reaction. After distilling off methylene chloride, the resulting aqueous suspension is refluxed for 30 minutes and then cooled to room temperature. The resulting crystals are separated by filtration and the wet crystals are dried at 60° C. to give the crude product (58.33 g). To the crude product (29.17 g) are added 2.5 mol/L aqueous sodium hydroxide solution (400 mL) and toluene (100 mL), and insoluble materials are removed by filtration and then separated into two layers. The aqueous layer is washed twice with toluene (100 mL) and neutralized with 6 mol/L hydrochloric acid (300 mL). The precipitated crystals are separated by filtration and dried at 60° C. and then recrystallized from methanol (540 mL) to give the desired product (19.67 g, yield 65.8%, purity by HPLC 99.4%).

$^1$H NMR (300 MHz, DMSO-d$_6$): δ=2.39 (3H, s), 2.53 (3H, s), 7.31 (br.t, J=7.1 Hz), 7.32 (1H, d, J=7.2 Hz), 7.41 (1H, br.t, J=7.2 Hz), 7.47 (1H, d, J=7.2 Hz), 7.68 (br.d, J=8.2 Hz), 7.69 (1H, s), 7.86 (1H, d, J=8.2 Hz), 10.50 (1H, s), 12.6 (1H, br.s)

M.p. 231.3-232.6° C., white powdery.

The purity is measured by high performance liquid chromatography (HPLC) under the following conditions:

Detector: Ultraviolet absorptiometer (wavelength, 254 nm), YMC-Pack ODS-A A-312, mobile phase: 3 mmol/L sodium laurylsulfate solution/acetonitrile/phosphoric acid solution 600:400:1), column temperature: at a constant temperature of around 25° C.

Example 6

Preparation of 2-methyl-4-(2-methylbenzoylamino)benzoic acid

A toluene solution of a mixture of 2-chloro-2'-methyl-4'-(2-methylbenzoylamino)acetophenone and 2-chloro-4'-methyl-2'-(2-methylbenzoylamino)acetophenone obtained in the above Reference Example 5 is concentrated and to the residue is added isopropyl alcohol (twice volume). To the mixture is added dropwise an aqueous sodium hypochlorite solution (twice molar amount) at 10-20° C. After completion of the reaction (30 minutes to one hour), the reaction mixture is acidified with hydrochloric acid, and the precipitated crystals are separated by filtration to give a crude product of 2-methyl-4-(2-methylbenzoylamino)benzoic acid in a yield of 86-100%. This crude product is recrystallized from methanol to give the desired product (yield 57%, purity by HPLC 99.3%).

$^1$H NMR (300 MHz, DMSO-d$_6$): δ=2.39 (3H, s), 2.53 (3H, s), 7.31 (br.t, J=7.1 Hz), 7.32 (1H, d, J=7.2 Hz), 7.41 (1H, br.t, J=7.2 Hz), 7.47 (1H, d, J=7.2 Hz), 7.68 (1H, br.d, J=8.2 Hz), 7.69 (1H, s), 7.86 (1H, d, J=8.2 Hz), 10.50 (1H, s), 12.6 (1H, br.s)

M.p. 231.3-232.6° C., while powder.

The purity is measured by high performance liquid chromatography (HPLC) under the following conditions:

Detector: Ultraviolet absorptiometer (wavelength, 254 nm), YMC-Pack ODS-A A-312, mobile phase: 3 mmol/L sodium laurylsulfate solution/acetonitrile/phosphoric acid solution 600:400:1), column temperature: at a constant temperature of around 25° C.

The invention claimed is:

1. A process for producing a benzazepine compound of the formula (1):

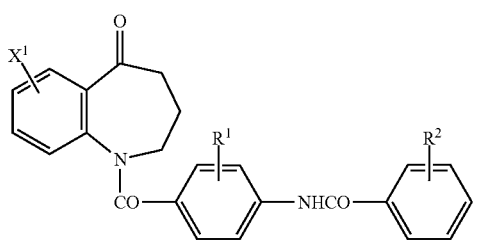

(1)

wherein $X^1$ is a halogen atom, $R^1$ and $R^2$ are independently a lower alkyl group, or salts thereof, which comprises reacting a benzazepine compound of the formula (2):

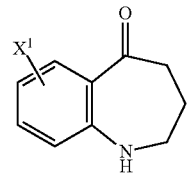

(2)

wherein $X^1$ is as defined above, or a salt thereof with an amide compound of the formula (3):

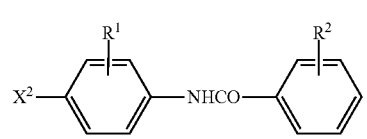

(3)

wherein $R^1$ and $R^2$ are as defined above and $X^2$ is a halogen atom, or a salt thereof in the presence of a carbonylating agent.

2. A process for producing a benzoic acid compound of the formula (4):

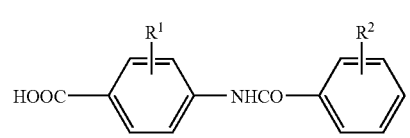

(4)

wherein $R^1$ and $R^2$ are independently a lower alkyl group, or a salt thereof, which comprises reacting an amide compound of the formula (11):

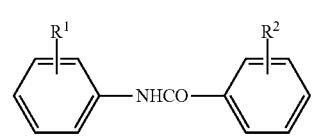

(11)

wherein $R^1$ and $R^2$ are as defined above, or a salt thereof, with a compound of the formula (19):

$X^6COCOX^7$ (19)

wherein $X^6$ and $X^7$ are independently a halogen atom.

3. A process for producing a benzoic acid compound of the formula (4):

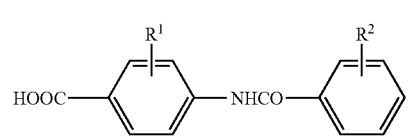

(4)

wherein $R^1$ and $R^2$ are independently a lower alkyl group, or a salt thereof, which comprises oxidizing an amide compound of the formula (12):

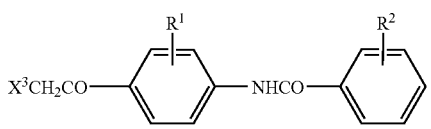

wherein $R^1$ and $R^2$ are as defined above and $X^3$ is a halogen atom, or a salt thereof.

4. A process for producing a benzoic acid compound of the formula (4):

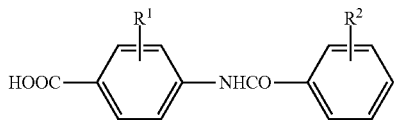

wherein $R^1$ and $R^2$ are independently a lower alkyl group, or a salt thereof, which comprises hydrolyzing an amide compound of the formula (13):

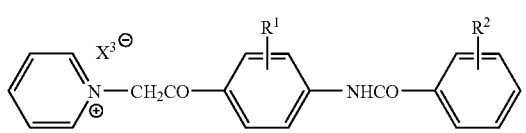

wherein $R^1$ and $R^2$ are as defined above and $X^3$ is a halogen atom, or a salt thereof.

5. A process for producing a benzoic acid compound of the formula (4):

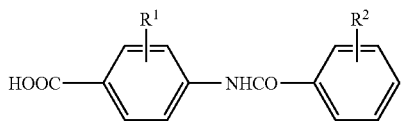

wherein $R^1$ and $R^2$ are independently a lower alkyl group, or a salt thereof, which comprises oxidizing an amide compound of the formula (14):

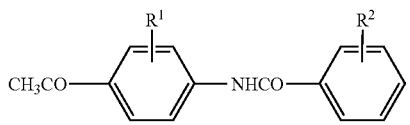

wherein $R^1$ and $R^2$ are as defined above, or a salt thereof.

6. A process for producing a 2,3,4,5-tetrahydro-1H-1-benzazepine compound of the formula (10):

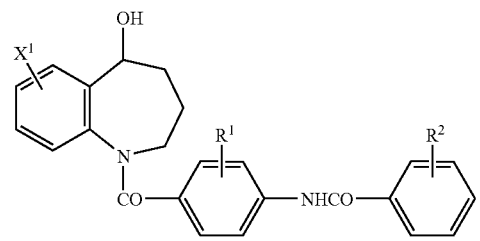

wherein $X^1$ is a halogen atom, $R^1$ and $R^2$ are independently a lower alkyl group, or a salt thereof, which comprises reducing a benzazepine compound of the formula (1):

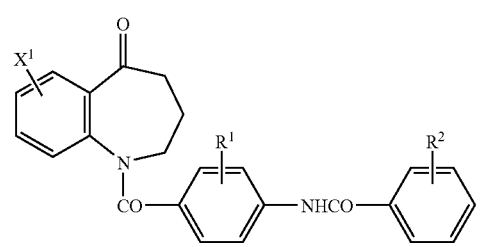

wherein $R^1$, $R^2$ and $X^1$ are as defined above, or a salt thereof in the presence of a hydrogenating agent selected from the group consisting of lithium aluminum hydride, sodium borohydride, zinc borohydride, and diborane in an amount of 0.25 to 1 mole per 1 mole of the compound (1).

7. The process according to claim 6, wherein the hydrogenating agent is sodium borohydride which is used in an amount of 0.25 to 1 mole per 1 mole of the compound (1).

8. The process according to claim 7, wherein the hydrogenating agent is used in an amount of 0.25 to 0.5 mole per 1 mole of the compound (1).

9. The process according to claim 1, wherein the benzazepine compound (1) is 7-chloro-1-[2-methyl-4-(2-methylbenzoylamino)benzoyl]-2,3,4,5-tetrahydro-1H-1-benzazepin-5-one, or a salt thereof.

10. The process according to any one of claims 6, 7 and 8, wherein the 2,3,4,5-tetrahydro-1H-1-benzazepine compound (10) is 7-chloro-5-hydroxy-1-[2-methyl-4-(2-methylbenzoylamino)benzoyl]-2,3,4,5-tetrahydro-1H-1-benzazepine, or a salt thereof.

11. A benzazepine compound selected from 7-chloro-5-hydroxy-1-{2-methyl-4-[N-(2-methylbenzoyl)-N-(2-methyl-4-(2-methylbenzoylamino)benzoylamino]benzoyl}-2,3,4,5-tetrahydro-1H-1-benzazepine (Compound A) or a salt thereof, 7-chloro-5-hydroxy-1-{2-methyl-4-[2-methyl-4-(2-methylbenzoylamino)benzoylamino]-benzoyl}-2,3,4,5-tetrahydro-1H-1-benzazepine (Compound B) or a salt thereof, 7-chloro-5-[2-methyl-4-(2-methylbenzoylamino)benzoyloxy]-1-[2-methyl-4-(2-methylbenzoylamino)benzoyl]-2,3-dihydro-1H-1-benzazepine (Compound C) or a salt thereof, or 7-chloro-5-[2-methyl-4-(2-methylbenzoylamino)benzoyloxy]-1-[2-methyl-4-(2-methylbenzoyl-amino)benzoyl]-2,3,4,5-tetrahydro-1H-1-benzazepine (Compound D) or a salt thereof.

* * * * *